(12) United States Patent
Miyawaki et al.

(10) Patent No.: US 8,182,987 B2
(45) Date of Patent: May 22, 2012

(54) PROBE FOR VISUALIZING CELL-CYCLE

(75) Inventors: Atsushi Miyawaki, Wako (JP); Asako Sawano, Wako (JP); Hisao Masai, Tokyo (JP)

(73) Assignees: Tokyo Metropolitan Institute of Medical Science, Tokyo (JP); Riken, Saitama (JP)

( * ) Notice: Subject to any disclaimer, the term of this patent is extended or adjusted under 35 U.S.C. 154(b) by 281 days.

(21) Appl. No.: 12/450,155

(22) PCT Filed: Feb. 6, 2008

(86) PCT No.: PCT/JP2008/051973
§ 371 (c)(1),
(2), (4) Date: Sep. 14, 2009

(87) PCT Pub. No.: WO2008/114544
PCT Pub. Date: Sep. 25, 2008

(65) Prior Publication Data
US 2010/0100977 A1  Apr. 22, 2010

(30) Foreign Application Priority Data
Mar. 16, 2007 (JP) .................. 2007-068240

(51) Int. Cl.
*C12N 15/63* (2006.01)
*C12Q 1/68* (2006.01)
*G01N 33/53* (2006.01)
*G01N 33/542* (2006.01)

(52) U.S. Cl. ............. 435/6.1; 435/320.1; 435/6.13; 435/7.9

(58) Field of Classification Search ............. None
See application file for complete search history.

(56) References Cited

U.S. PATENT DOCUMENTS
5,625,048 A  4/1997  Tsien et al.
6,124,128 A  9/2000  Tsien et al.

FOREIGN PATENT DOCUMENTS
WO  WO 96/23810  8/1996

OTHER PUBLICATIONS

Kudo et al (The Journal of Biological Chemistry, 1997. vol. 272, No. 47, pp. 29742-29751).*
Wohlschlegel et al (Science. Dec. 22, 2000; 290: 2309-2312).*
Kudo et al (Journal of Biological Chemistry. 1997; 272(47): 29742-29751).*
Nishitani et al (Journal of Biological Chemistry. 2004; 279(29): 30807-30816).*
Saxena et al (Molecular Cell. 2004; 15:245-258).*
European Search Report in corresponding European Application No. 08710869.2 dated Apr. 28, 2010.
Yoshida et al., "Peptide binding to Geminin and inhibitory for DNA replication," Biochemical and Biophysical Research Communications, vol. 317, pp. 218-222 (Apr. 23, 2004).
Benjamin et al., "Geminin has dimerization, Cdt1-binding, and destruction domains that are required for biological activity," The Journal of Biological Chemistry, vol. 279, No. 44, pp. 45957-45968 (Oct. 29, 2004).
Xouri et al., "Cdt1 and geminin are down-regulated upon cell cycle exit and are overexpressed in cancer-derived cell lines," Eur. J. Biochem., vol. 271, pp. 3368-3378 (Aug. 16, 2004).
Nishitani et al., "Control of DNA replication licensing in a cell cycle," Genes to Cells, vol. 7, pp. 523-534 (Jun. 1, 2002).
Tada, "Cdt1 and geminin: role during cell cycle progression and DNA damage in higher eukaryotes," Frontiers in Bioscience, vol. 12, pp. 1629-1641 (Jun. 1, 2007).
Spella et al., "Licensing regulators geminin and Cdt1 identify progenitor cells of the mouse CNS in a specific phases of the cell cycle," Neuroscience, vol. 147, pp. 373-387 (Jun. 19, 2007).
Haraguchi, "Visualization of dynamics of nucleoproteins in a cell cycle . . . ", Japan Society of Histochemistry and Cytochemistry Sokai, Gakujutsu Shukai Program, Yokoshu, vol. 40, p. 125, WSI-5 (1999).
Yamauchi et al., "Visualization and Quantitative Analysis for Intracellular Events . . . ", Biophysics, vol. 45, No. 3, pp. 153-156 (2005).
Ito et al., "Epstein-Barr virus nuclear antigen-1 is highly colocalized . . . ", Journal of General Virology, vol. 83, No. 10, pp. 2377-2383 (2002).
Rebollo et al., "Visualizing the spindle checkpoint in . . . ", EMBO Reports, vol. 1, No. 1, pp. 65-70 (2000).
Carminati et al., "Microtubules Orient the Mitotic Spindle . . . ", The Journal of Cell Biology, vol. 138, No. 3, pp. 629-641 (1997).
Ballabeni et al., "Human Geminin promotes pre-RC formation . . . ", The EMBO Journal, vol. 23, No. 15, pp. 3122-3132 (2004).
Lee et al., "Structural basis for inhibition of the . . . ", Nature, vol. 430, No. 7002, pp. 913-917 (2004).
Sakaue-Sawano et al., "Visualizing Spatiotemporal Dynamics . . . ", Cell, vol. 132, No. 3, pp. 487-498 (2008). Ward et al., "Spectral Perturbations of the *Aequorea* . . . ", Photochem. Photobiol., vol. 35, pp. 803-808 (1982).
Levine et al., "Isolation and Characterization of a Photoprotein . . . ", Comp. Biochem. Physiol., vol. 72B, pp. 77-85 (1982).
Prasher et al., "Primary structure of the *Aequorea victoria* . . . ", Gene, vol. 111, pp. 229-233 (1992).
Heim et al., "Wavelength mutations and posttranslational autoxidation . . . ", Proc. Natl. Acad. Sci. USA, vol. 91, pp. 12501-12504 (1994).
Heim et al., "Engineering green fluorescent protein for . . . ", Current Biology, vol. 6, No. 2, pp. 178-182 (1996).
Tsien, "The Green Fluorescent Protein", Annu. Rev. Biochem., vol. 67, pp. 509-544 (1998).
Hoffman et al., "Whole-body imaging with fluorescent proteins", Nature Protocols, vol. 1, No. 3, pp. 1429-1438 (2006).

(Continued)

*Primary Examiner* — Scott Long
(74) *Attorney, Agent, or Firm* — Harness, Dickey & Pierce, P.L.C.

(57) ABSTRACT

An object of an embodiment of the present invention is to provide a method with which it is possible to easily distinguish a proliferation phase of a cell cycle from a resting phase thereof in real time. The object of the embodiment of the present invention is attained by providing a method for performing phase identification of the cell cycle, the method including: visualizing one or more gene-expression products as markers whose amounts in a cell change in a cell-cycle dependent manner; and detecting the products so as to distinguish the proliferation phase of the cell cycle from the resting phase thereof.

9 Claims, 10 Drawing Sheets

OTHER PUBLICATIONS

Miyata et al., "Visualization of Cell Cycling by an Improvement . . . ", J. Neurosci. Res., vol. 69, pp. 861-868 (2002).
Leonhardt et al., "Dynamics of DNA Replication Factories . . . ", The Journal of Cell Biology, vol. 149, No. 2, pp. 271-279 (2000).
Jackman et al., "Cyclin A- and Cyclin E-Cdk Complexes . . . ", Molecular Biology of the Cell, vol. 13, pp. 1030-1045 (2002).
Jackman et al., "Active cyclin B1-Cdk1 first appears . . . ", Nature Cell Biology, vol. 5, pp. 143-148 (2003).
Thomas, "Lighting the Circle of Life", Cell Cycle, vol. 2, Issue 6, pp. 545-549 (2003).
Zhang et al., "Bioluminescent imaging of Cdk2 inhibition in vivo", Nature Medicine, vol. 10, No. 6, pp. 643-648 (2004).
Thomas et al., "Characterization and Gene Expression Profiling . . . ", Cell Cycle, vol. 4, Issue 1, pp. 191-195 (2005).
Easwaran et al., "Cell Cycle Markers for Live Cell Analyses", Cell Cycle, vol. 4, Issue 3, pp. 453-455 (2005).
Kisielewska et al., "GFP-PCNA as an S-phase marker in . . . ", Biol. Cell., vol. 97, pp. 221-229 (2005).
Essers et al., "Nuclear Dynamics of PCNA in DNA Replication and Repair", Molecular and Cellular Biology, vol. 25, No. 21, pp. 9350-9359 (2005).
Kitamura et al., "Live-Cell Imaging Reveals Replication of Individual . . . ", Cell, vol. 125, pp. 1297-1308 (2006).
Xouri et al., "Cdt1 associates dynamically with chromatin . . . ", The EMBO Journal, vol. 26, No. 5, pp. 1303-1314 (2007).
Sakaue-Sawano et al., "Tracing of the Silhouette of Individual Cells in . . . ", Chemistry & Biology, vol. 15, pp. 1243-1248 (2008).
Hahn et al., "Quantitative analysis of cell cycle phase . . . ", Cell Cycle, vol. 8, No. 7, pp. 1044-1052 (2009).
Hiraoka et al., "Multispectral Imaging Fluorescence . . . ", Cell Structure and Function, vol. 27, pp. 367-374 (2002).
Miyawaki et al., "Lighting up cells: labeling . . . ", Nat. Cell Biol. Suppl., pp. S1-S7 (2003).
Ang et al., "Interwoven Ubiquitination Oscillators . . . ", Sci. STKE (242) pe31, pp. 1-5 (2004).
Giepmans et al., "The Fluorescent Toolbox for Assessing . . . ", Science, vol. 312, pp. 217-224 (2006).
Tsien et al., "Constructing and Exploiting the Fluorescent . . . ", Angew. Chem. Int. Ed., vol. 48, pp. 5612-5626 (2009).
"G2M Cell Cycle Phase Marker Assay"—Amersham Biosciences, User Manual, 25-8010-50UM, Rev-A (2003).
"G1S Cell Cycle Phase Marker Assay"—Amersham Biosciences, User Manual, 25-9003-97UM, Rev-A (2005).

* cited by examiner

FIG. 3
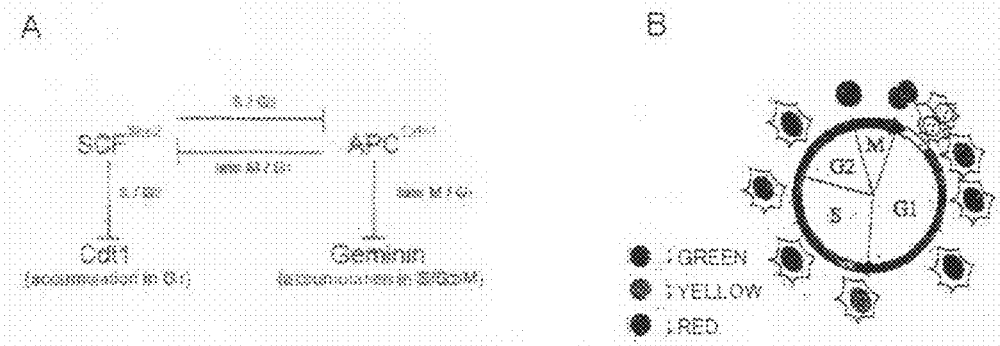
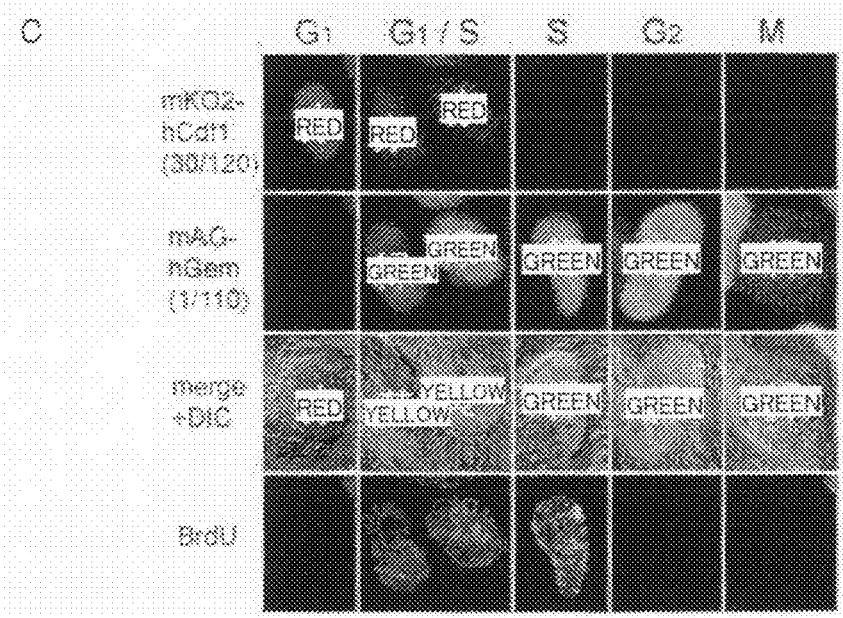
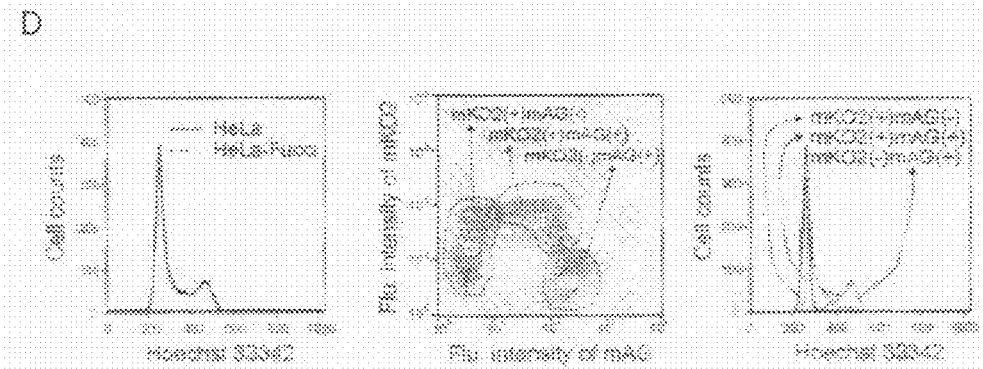

PROBE FOR VISUALIZING CELL-CYCLE

TECHNICAL FIELD

The present invention relates to (i) a method for performing phase identification of a cell cycle by visualizing, by using a marker, a gene-expression product whose amount in a cell changes in a cell-cycle dependent manner and (ii) a gene construct for use in the method.

BACKGROUND ART

A cell cycle is a process in which a cell produced by a cell division undergoes another cell division to produce a new cell. Of the cell cycle, a phase during which mitosis takes place is called an M phase. Generally, the M phase completes in approximately one hour. An interval between one M phase and another M phase is called an interphase during which cell growth as well as biosynthesis and/or metabolism of a substance occur. The interphase can be further divided into a G1 phase, an S phase, and a G2 phase. In the S phase, DNA replication takes place. The G1 phase is a phase between the M phase and the S phase, and the G2 phase is a phase between the S phase and the M phase.

As a method for analyzing a specific phase of the cell cycle (G1 phase, S phase, G2 phase, or M phase), a method using a BrdU label is known. In specific, the method includes: causing a BrdU to be taken into a cell for a given period; and subsequently, carrying out immunohistochemistry by using an anti-BrdU antibody. However, with the method, it is impossible to carry out observation in real-time. There is also known a method using cell synchronization and a biochemical model. With the method, however, it is impossible to carry out real-time observation.

As a method for visualizing a specific phase of the cell cycle, there is a method using the G2M cell cycle phase marker (G" MCCPM) (Amersham Bioscience K.K). Because the method uses promoter activity of cyclin, there is a problem in that transformation by gene introduction is remarkably influenced depending on how a transgene is integrated into a chromosome. Further, because the G1 phase is not visualized, (i) it is difficult to track a cell cycle, and (ii) a contrast is unclear.

SUMMARY OF INVENTION

Problem to be Solved by the Invention

An object of the present invention is to provide a method for performing phase identification of a cell cycle, by which method it is possible to easily distinguish a proliferation phase of the cell cycle from a resting phase thereof in real time. The present invention further has an object to provide a gene construct for use in the method of the present invention.

Solution to Problem

The inventors of the present invention made a diligent study in order to attain the aforementioned objects of the present invention. As a result, the inventors found it possible to distinguish a proliferation phase of a cell cycle from a resting phase thereof by (i) visualizing, by using a marker, at least one or more gene-expression products whose amounts in a cell change in a cell-cycle dependent manner and (ii) detecting the marker. By this, the inventors of the present invention accomplished the present invention.

Namely, the present invention provides the following:

(1) a method for performing phase identification of a cell cycle, the method including the steps of: visualizing, by using a marker, at least one or more gene-expression products whose amounts in a cell change in a cell-cycle dependent manner; and detecting the marker so as to distinguish a proliferation phase of the cell cycle from a resting phase of the cell cycle;

(2) the method as set forth in aspect 1, wherein the at least one or more gene-expression products are at least two or more gene-expression products whose amounts in the cell change in cell-cycle dependent manners different from one another.

(3) the method as set forth in aspect 1 or 2, wherein as the at least one or more gene-expression products, a gene-expression product whose amount changes in a G1 phase and an S/G2/M phase including an S phase, a G2 phase, and a M phase is used.

(4) the method as set forth in any one of aspects 1 through 3, wherein the at least one or more gene-expression products are (i) a first gene-expression product whose amount increases in a G1 phase and decreases in an S/G2/M phase and (ii) a second gene-expression product whose amount decreases in the G1 phase and increases in the S/G2/M phase, and the first gene-expression product and the second gene-expression product are labeled by the markers different from each other, so as to visualize the first gene-expression product and the second gene-expression product.

(5) the method as set forth in aspect 4, wherein the first gene-expression product is Cdt1 or a partial fragment of Cdt1, and the second gene-expression product is Geminin or a partial fragment of Geminin.

(6) the method as set forth in aspect 5, wherein the first gene-expression product is the partial fragment of Cdt1, which partial fragment of Cdt1 is remaining of Cdt1 from which a Geminin binding site is excluded.

(7) the method as set forth in aspect 5 or 6, wherein the first gene-expression product is the partial fragment of Cdt1, which partial fragment of Cdt1 is composed of 30th through 120th amino acids of Cdt1.

(8) the method as set forth in any one of aspects 5 through 7, wherein the second gene-expression product is the partial fragment of Geminin, which partial fragment of Geminin is remaining of Geminin from which a Cdt1 binding site is excluded.

(9) the method as set forth in any one of aspects 5 through 8, wherein the second gene-expression product is the partial fragment of Geminin, which partial fragment of Geminin is composed of 1st through 110th amino acids of Geminin.

(10) the method as set forth in any one of aspects 1 through 9, wherein the marker is a fluorescent protein or a luminescent protein.

(11) a gene construct, including (i) a gene for or a partial fragment of a gene for an expression product whose amount in a cell changes in a cell-cycle dependent manner and (ii) a gene encoding a marker.

(12) the gene construct as set forth in aspect 11, wherein the gene for the expression product whose amount in the cell changes in the cell-cycle dependent manner is a Cdt1 gene or a Geminin gene.

(13) the gene construct as set forth in aspect 11 or 12, wherein the partial fragment of the gene for the expression product whose amount in the cell changes in the cell-cycle dependent manner is (i) a gene encoding a partial fragment of Cdt1, which partial fragment of Cdt1 is remaining of Cdt1 from which a Geminin binding site is excluded, or (ii) a gene coding for a partial fragment of Geminin, which partial fragment of Geminin is remaining of Geminin from which a Cdt1 binding site is excluded.

(14) the gene construct as set forth in aspect 13, wherein the partial fragment of the gene for the expression product whose amount in the cell changes in the cell-cycle dependent manner is (i) a gene fragment encoding a partial fragment of Cdt1 composed of 30th through 120th amino acids of Cdt1 or (ii) a gene fragment encoding a partial fragment of Geminin composed of 1st through 110th amino acids of Geminin.

(15) the gene construct as set forth in any one of aspects 11 through 14, wherein the gene encoding the marker is (i) a gene encoding a fluorescent protein or (ii) a gene encoding a luminescent protein.

(16) a transformant, comprising a gene construct as set forth in any one of aspects 11 through 15.

(17) a transgenic nonhuman animal, including a gene construct as set forth in any one of aspects 11 through 15.

(18) a method for performing phase identification of a cell cycle, the method including the steps of: introducing, into a cell, at least one or more gene constructs as set forth in any one of aspects 11 through 15; expressing (i) the gene for or the partial fragment of the gene for the expression product whose amount in the cell changes in the cell-cycle dependent manner, and (ii) the marker; and detecting the marker so as to distinguish a proliferation phase of the cell cycle from a resting phase of the cell cycle.

(19) a method for screening a cell-cycle inhibitor or a drug for a cell cycle-related disease or a method for examining a compound, a drug, or a reagent on its effect and a functional mechanism, the method including the steps of: incubating a cell in the presence of a candidate substance for the cell-cycle inhibitor, a candidate substance for the drug for the cell cycle-related disease, or a reagent for inhibiting specific gene expression; and performing phase identification of a cell cycle in accordance with a method as set forth in any one of aspects 1 through 10 or 18, so as to select a candidate substance which has an influence on the cell cycle and/or cell death.

(20) a method for screening a drug for a disease or a method for examining a compound, a drug, or a reagent on its effect and a functional mechanism, the method including the steps of: administrating, to a transgenic nonhuman animal as set forth in aspect 17, a candidate substance for a cell-cycle inhibitor, a candidate substance for a drug for a cell cycle-related disease, or a reagent for inhibiting specific gene expression; and selecting a candidate substance which has an influence on proliferation of a tumor in the transgenic nonhuman animal or on a cell cycle, survival, or the like of a cell in an immune system, a hematocyte system, or the like system in the transgenic nonhuman animal.

Advantageous Effects of Invention

With the present invention, it is possible to easily distinguish a proliferation phase of a cell cycle from a resting phase thereof in real-time. The present invention provides a probe, by use of which G1/S transition (transition from a G1 phase to an S phase, which transition is the most important in considering control of a cell cycle) can be detected as a color conversion from a red color to a green color (a contrast between red and green colors is higher than a contrast between any other colors). In particular, because the method of the present invention does not use cell-cycle dependent gene transcription (promoter), a permanent promoter can be used, thereby making it possible to easily produce a transgenic organism.

Furthermore, the present invention is arranged so that a signal for a cell cycle is localized in a nucleus, thereby making it possible that the probe of the present invention be expressed at the same time with various fluorescent probes working in a cytoplasm. The present invention makes it possible to study how the cell cycle is coordinated with various cell functions.

BRIEF DESCRIPTION OF DRAWINGS

FIG. 3 shows an experiment in which a mechanism of and performance assessment of a Fucci probe are studied.

DESCRIPTION OF EMBODIMENTS

Figure 1:
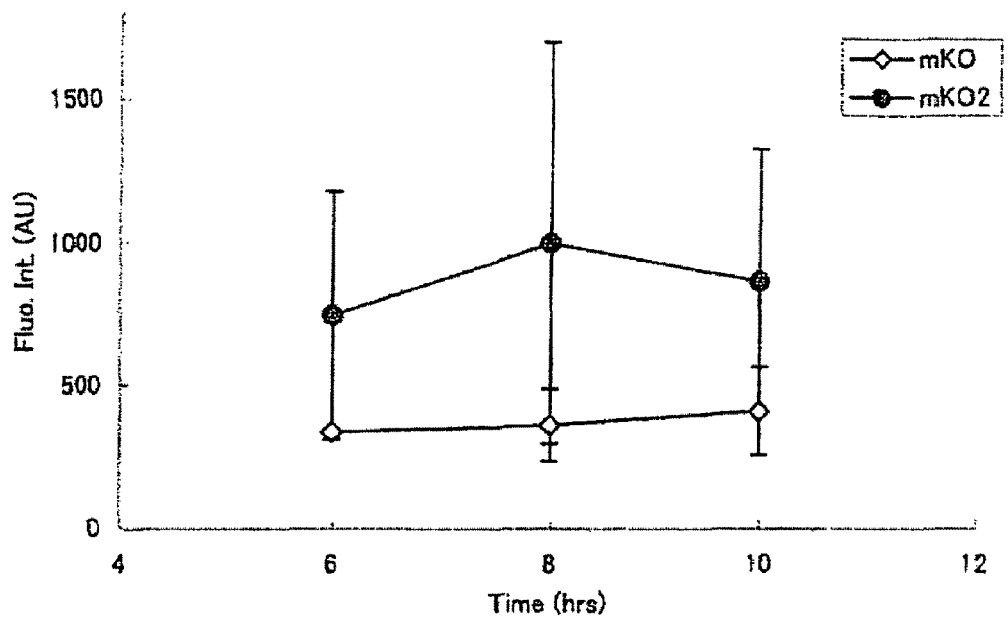
FIG. 1 is a graph showing a result obtained by comparing mKO and mKO2 in terms of fluorescent brightness.

An embodiment of the present invention is explained in detail below.

A method in accordance with the present invention for performing phase identification of a cell cycle is a method which includes: visualizing, by marking with a marker, at least one or more gene-expression products whose amounts in a cell change in a cell-cycle dependent manner; and detecting the marker so as to distinguish a proliferation phase of a cell cycle from a resting phase thereof.

In the present specification, a G1 phase is a prereplicative resting-phase (which is simply referred to as a "resting phase" herein), and an S/G2/M phase is a DNA synthesis/cell division phase (which is simply referred to as a "proliferation phase" herein).

In the present invention, it is preferable that at least one or more gene-expression products above be at least two or more gene-expression products whose amounts in the cell change in cell-cycle dependent manners different from one another. It is particularly preferable that as at least one or more gene-expression products above, a gene-expression product whose amount in a cell changes in the G1 phase and the S/G2/M phase be used. In specific, as at least one or more gene-expression products above, (i) a first gene-expression product whose amount increases in the G1 phase and decreases in the S/G2/M phase and (ii) a second gene-expression product whose amount decreases in the G1 phase and increases in the S/G2/M phase can be used.

Concrete examples of the first gene-expression product whose amount increases in the G1 phase and decreases in the S/G2/M phase encompass p27, p57, p21, p130, Cyclin A, Cyclin D, Cyclin E, CDK9, MYC, E2F1, ORC1, CDT1, B-MYB, RAG2, SMAD4, FOXO1, UBP43, Viral E7, Notch1, Notch 4, JUN, Presenilin ½, SREBP ½, β-catenin, IκBα/β/ε, p105/p100, Cdc25 A/B, Wee1A, EMI ½, Viral Vpu, ATF4, DIG1, INFα-R, PRL-R, Snail, PER ½, Claspin and the like, to which the present invention is not limited. Among them, Cdt1 or a partial fragment thereof are preferable. The partial fragment of Cdt1 can be a partial fragment obtained by removing a Geminin binding site from Cdt1.

Concrete examples of the gene-expression product whose amount decreases in the G1 phase and increases in the S/G2/M phase encompass Cyclin A, Cyclin B, CDC20, PLK1, Aurora A/B, NEK2A, mE2-C, Geminin, CDC6, SKP2, SNON, RRR2, TK1, TPX2, CDH1, Securin, KIP, Survivin, Dbf 4, Hsl 1, Sgo 1, Sororin, R2, UBCH10/E2-C/Vihar, Cks 1, Ase 1/Prc 1, Cin 8, Anillin, and the like, to which the present invention is not limited t. Among them, Geminin or a fragment thereof is preferable. A partial fragment of Geminin can be a partial fragment obtained by removing a Cdt1 binding site from Geminin.

The gene-expression products can be visualized by being labeled with a marker. In a case where two or more gene-expression products are used, they are labeled with different markers, respectively, so as to be visualized. For the marker to be used in the present invention, a fluorescent protein or a luminescent protein is preferable. It is preferable that the fluorescent protein or the luminescent protein to be used in the present invention be a protein which (i) quickly acquires fluorescence activity or luminescence activity and (ii) is degraded along with degradation of a protein (the gene-expression product) to which the fluorescent protein or the luminescent protein (marker) is fused, and rapidly loses the fluorescence activity or the luminescent activity.

As the fluorescent protein, a variety of fluorescent proteins are cloned typically from a cnidarian, hydrozoa, *Aequorea-victoria* derived *Aequorea*GFP (Green Fluorescent Protein), and also from other organisms such as anthozoa (coral and actinia), hydrozoa other than *Aequorea Victoria*, anthropod and crustacea, and the like. Further, as the fluorescent protein, a variant obtained by inducing a mutation into any of the above fluorescent proteins is reported.

In the present invention, for example, a green fluorescent protein (GFP) of cnidarian or a variant of a green fluorescent protein (GFP) of cnidarian can be used. Examples of such variants can include cyan fluorescent protein (CFP), yellow fluorescent protein (YFP), red fluorescent protein (RFP), blue fluorescent protein (BFP), and the like. These fluorescent proteins can be obtained from Pacific Northwest jellyfish, *Aequorea victoria*, the sea pansy, *Renilla reniformis, Phialidium gregarium*, and the like (Ward, W. W., et al. Photochem. Photobiol., 35:803-808 (1982); and Levine, L. D., et al. Comp. Biochem. Physiol., 72B: 77-85 (1982)). Various types of jellyfish-derived fluorescent proteins having a useful excitation spectrum and an emittance spectrum are produced by altering an amino-acid sequence of *Aequorea Victoria*-derived natural GFP (Prasher, D. C., et al. Gene, 111:229-233 (1992); Heim, R., et al. Proc. Natl. Acad. Sci., USA, 91:12501-04 (1994); U.S. patent application Ser. No. 08/337,915; PCT international No. PCT/US95/14692; and U.S. patent application Ser. No. 08/706,408). Further, a GFP variant, whose excitation wavelength or emission wavelength is shifted due to induction of mutation, is produced (Heim, R. & Tsien, R. Y. Current Biol. 6:178-182 (1996)). Plural reports on cloning of a fluorescent protein are made and described in, for example, (i) "Primary structure of the *Aequorea victoria* green fluorescent protein" (Prasher, D. C., et al. Gene 111: 229-233 (1992)), (ii) Annu. Rev. Biochem. 1998 (Roger Y. Tsin. 67:509-44), (iii) references cited in the respective literatures, and (iv) the like literatures.

Concrete examples of the fluorescent protein and the luminescent protein usable in the present invention are shown below. However, neither the fluorescent protein nor the luminescent protein usable in the present invention is limited to the examples.

TABLE 1

| Color | Name of Fluorescent Protein | Seller |
|---|---|---|
| Blue | mCGFP | |
| | BFP | |
| | EBFP | |
| | sgBFP | Q-BIOgene |
| | CFP | |
| | ECFP | |
| | mECFP | |
| | Cerulean | |
| | PS-CFP (PS-CFP2) | EVRΩGEN |
| | amajGFP:amFP486 (AmCyan1) | Clontech (TAKARA) |
| | Midoriishi-Cyan (MiCy) | MBL (Amalgaam) |

TABLE 2

| Color | Name of Fluorescent Protein | Seller |
|---|---|---|
| Green | Aequorea GFP | |
| | S65T | |
| | EGFP | |
| | Emerald (EmGFP) | Invitrogen |
| | SgGFP | Q-BIOgene |
| | Sapphire | |
| | T-Sapphire | |
| | GFP uv | |
| | PA-GFP | |
| | aceGFP (AceGFP) | EVRΩGEN |
| | *Renilla* GFP (hrGFP) | STRATAGENE |
| | hr GFP II | STRATAGENE |
| | MGFP (hMGFP) | Promega |
| | mHoneydew | |
| | zoan GFP: zFP506(ZsGreen 1) | Clontech (TAKARA) |
| | E5 (Fluorescent Timer) | Clontech (TAKARA) |
| | Kaede | MBL (Amalgaam) |
| | Azami-Green (AG) | MBL (Amalgaam) |
| | mAG | MBL (Amalgaam) |
| | EosFP | |
| | mEosFP | |
| | 22G | |
| | Dronpa (Dronpa-Green) | MBL (Amalgaam) |
| | KiKG | |
| | KiKGR | MBL (Amalgaam) |
| | ppluGFP2 (CopGFP)(TurboGFP) | EVRΩGEN |

TABLE 3

| Color | Name of Fluorescent Protein | Seller |
|---|---|---|
| Yellow | YFP | |
| | EYFP | |
| | Citrine | |
| | mEYFP | |
| | Venus | |
| | mVenus | |
| | Topaz (YFP) | Invitrogen |
| | PhiYFP | EVRΩGEN |
| | PhiYFP-m | EVRΩGEN |
| | mBanana | |
| | zoan YFP: zFP538 (ZsYellow1) | Clontech (TAKARA) |

TABLE 4

| Color | Name of Fluorescent Protein | Seller |
| --- | --- | --- |
| Red | mOrange | |
| | mTangerine | |
| | OFF (cOFP) | STRATAGENE |
| | Kusabira-Orange (KO) | Medical & Biological Laboratories Co., Ltd. (MBL) (Amalgaam) |
| | mKO | MBL (Amalgaam) |
| | mKO2 | MBL (Amalgaam) |
| | JRed | EVRΩGEN |
| | DsRed: drFP583 | Clontech (TAKARA) |
| | DsRed-Monomer | Clontech (TAKARA) |
| | DsRed2 | Clontech (TAKARA) |
| | T1 | Clontech (TAKARA) |
| | dTomato | |
| | tdTomato | |
| | mRFP1 | |
| | mStrawberry | |
| | mCherry | |
| | mRasberry | |
| | mPlum | |
| | PA-mRFP1 | |
| | E57 | |
| | eqFP611 | |
| | HcRed1 | Clontech (TAKARA) |
| | HcRed1-tandem | EVRΩGEN |
| | KFP1 (KFP-Red) | EVRΩGEN |
| | asCP/A148S | |
| | AsRed2 | Clontech (TAKARA) |
| | AQ143 | |
| | Keima | MBL (Amalgaam) |

TABLE 5

| Name of Luminescent Protein | Biological origin |
| --- | --- |
| Luciferase (Luc) | firefly |
| | *Renilla* |
| | click beetle |

The present invention provides a gene construct which includes (i) a gene for or a partial fragment of a gene for an expression product whose amount in the cell changes in a cell-cycle dependent manner and (ii) a gene encoding the marker. It is possible that the gene construct of the present invention be used as a probe which uses protein degradation occurring in a cell-cycle dependent manner. The gene construct of the present invention can be constructed as follows: obtaining, in accordance with normal gene-recombination technologies, (i) the gene for or the partial fragment of the gene for the expression product whose amount in the cell changes in a cell-cycle dependent manner and (ii) the gene encoding the marker; and subsequently linking the gene for or the partial fragment of the gene for the expression product and the gene encoding the marker.

For example, a gene encoding a fluorescent protein can be obtained by: providing (i) a template DNA containing cDNA of the fluorescent protein and (ii) a primer corresponding to a DNA sequence of the fluorescent protein; and carrying out PCR by use of the template DNA and primer. Likewise, a gene for or a fragment of a gene for an expression product whose amount in a cell changes in a cell-cycle dependent manner can be obtained by: providing a primer corresponding to a DNA sequence of the gene; and carrying out PCR by use of the primer. In a case where a restriction enzyme site is introduced into the primer for use in amplifying a gene fragment by PCR, it is possible to insert an amplified product obtained by the PCR into a corresponding restriction enzyme site in a proper vector. By inserting, adjacently into a same vector, (i) the gene for or the partial fragment of the gene for the expression product whose amount in the cell changes in the cell-cycle dependent manner and (ii) the gene encoding the marker, it is possible to produce the gene construct including the gene for or the partial fragment of the gene for the expression product above and the gene encoding the marker.

A vector for use in the present invention is not limited to a particular kind. For example, the vector can be a vector (e.g., plasmid or the like) which autonomously replicates itself or a vector which is, when being introduced into a host cell, integrated into a genome of the host cell and replicated together with a chromosome of the host cell. Preferably, the vector for use in the present invention is an expression vector. In the expression vector, a gene of the present invention is arranged in such a way that elements (e.g., a promoter or the like) necessary for transcription are functionally linked to the gene. The promoter is a DNA sequence showing transcription activity in the host cell, and can be selected as appropriate based on a kind of the host cell.

According to the present invention, the gene construct obtained in the above way is introduced into a cell, and (i) the gene for or the partial fragment of the gene for the expression product above and (ii) the marker are expressed. By detecting the marker, it is possible to distinguish the proliferation phase of the cell cycle from the resting phase thereof, thereby making it possible to perform phase identification of the cell cycle.

Construction of the expression vector and introduction (transfection) thereof into a cell can be carried out in accordance with methods well known to a person skilled in the art. The details are described in "Molecular Cloning—A Laboratory Manual, Cold Spring Harbor Laboratory, Cold Spring Harbor, N.Y." (Sambrook, et al. 1989) and "Current Protocols in Molecular Biology" (Current Protocols, a joint venture between Greene Publishing Associates, Inc. and John Wiley & Sons, Inc., most recent Supplement) (F. M. Ausubel, et al., eds.).

For example, transfection can be carried out in accordance with a DNA transfection method such as a calcium phosphate coprecipitation method, microinjection, electroporation, insertion of a plasmid which has been introduced into a liposome or a virus vector, or the like.

The method in accordance with the present invention for performing phase identification of a cell cycle can be applied in, for example, a method for screening a drug (such as a cell-cycle inhibitor, a drug for a cell-cycle related disease, or the like drug). In specific, in accordance with the method of the present invention, phase identification of a cell cycle is performed onto a cell incubated in the presence of a drug candidate. This makes it possible to select a drug candidate having an influence on the cell cycle, thereby making it possible to screen the cell-cycle inhibitor, the drug for the cell-cycle related disease, or the like.

Furthermore, the present invention provides a transformant containing the gene construct. By introducing the gene construct of the present invention into a proper host cell, it is possible to produce the transformant. The host cell is not particularly limited in a kind, and examples of the host cell can encompass a bacterial cell, a yeast cell, a fungal cell, a higher eukaryotic cell, and the like cell. Examples of the bacterial cell can encompass Gram-positive bacteria, such as *bacillus, streptomyces*, and the like, and Gram-negative bacteria, such as *Escherichia coli* and the like. Examples of a mammalian cell can encompass an HEK293 cell, a HeLa cell, a COS cell, a BHK cell, a CHL cell, a CHO cell, and the like cell. A method for transforming a mammalian cell and expressing a DNA sequence introduced into the mammalian cell is also well known, and usable examples of the method encompass an electroporation method, a calcium phosphate transfection method, a lipofection method, and the like method. Examples of the yeast cell can encompass cells belonging to *saccharomyces* and those belonging to *schizosaccharomyces*, and examples of such cells can encompass *Saccharomyces cerevisiae, Saccharomyces kluyveri*, and the like. Examples of a method for introducing a recombinant vector into a yeast host can encompass an electroporation method, a spheroplast method, a lithium acetate method, and the like method. An example of other fungal cells is filamentous fungus, which is a cell belonging to, for example, *Aspergillus, Neurospora, Fusarium*, or *Trichoderma*. In a case where the host cell is one of the filamentous fungus, transformation can be performed by integrating a DNA construct into a host chromosome so as to produce a recombinant host cell. Integration of the DNA construct into the host chromosome can be carried out in a well known manner by use of, for example, homologous recombination or heterologous recombination.

Furthermore, the present invention provides a transgenic nonhuman animal having the above gene construct.

A method for producing the transgenic nonhuman animal of the present invention is not particularly limited. For example, the transgenic nonhuman animal of the present invention can be produced by introducing the gene construct of the present invention into a fertilized egg or the like. It is preferable that the gene construct of the present invention, which is used as a transgene in producing the transgenic nonhuman animal, be a recombinant gene produced by linking (i) the gene for or the partial fragment of the gene for the expression product whose amount in a cell changes in a cell-cycle dependent manner and (ii) the gene encoding the marker to a downstream of a proper mammalian promoter. The transgenic nonhuman animal of the present invention can be produced by, for example, (i) introducing the gene construct of the present invention into a fertilized egg of a nonhuman animal and (ii) implanting the fertilized egg into a pseudopregnant female nonhuman animal, so as to deliver a nonhuman animal in which the gene construct of the present invention has been introduced. Usable examples of the nonhuman animal are a rodent such as a mouse, a hamster, a guinea pig, a rat, a rabbit, and the like, and an animal such as a dog, a cat, a goat, a sheep, a bovine, a pig, a monkey, a zebrafish, a *drosophila*, and the like. In view of easiness of production, development, use, or the like, a rodent such as a mouse, a hamster, a guinea pig, a rat, a rabbit, and the like is more preferable, and among them, a mouse is the most preferable.

After it is confirmed that members of the transgenic animal of the present invention stably posses the gene construct of the present invention after being produced by breeding, the transgenic animal of the present invention can be reared, as an animal having the gene, for generations in a normal rearing environment. A homozygous animal having a transgene in both pairs of a homologous chromosome is obtained, and a male and a female member of the homozygous animal are bred with each other. This makes it possible to breed the homologous animal for generations in such a manner that every descendant excessively possesses the transgene. In order to identify a site where (i) the gene for or the partial fragment of the gene for the expression product whose amount in the cell changes in the cell-cycle dependent manner and (ii) the gene encoding the marker are expressed, expression of the transgene can be observed at each of an individual level, an organ level, a tissue level, and a cellular level.

The present invention is described in detail below with reference to examples of experiment. However, the present invention is not limited to the examples.

EXAMPLES

Example 1

Construction of Plasmid (1) Construction of mKO2-Cdt1

(A) Development of Fluorescence Emission Ability Quick-Acquiring Variant of Fluorescent Protein Monomer Kusabira-Orange (mKO)

In a case where a fluorescent protein is used as a reporter in detecting a cell cycle phase and/or a physiological signal in a cell, it is necessary that the fluorescent protein emit fluorescence immediately after being translated. If there is a significant time gap between (i) occurrence of an event intended to be visualized and (ii) acquisition of fluoresce emission ability by the fluorescent protein, a detection model itself may become useless. In view of this, for the fluorescent protein to be used as the reporter, a variant (i.e., fluorescence emission ability quick-acquiring variant) which quickly matures after translation to acquire the fluorescence emission ability was produced. The variant was produced from mKO, which was a monomeric variant of a fluorescent protein Kusabira-Orange (KO) isolated from Fungia scutaria of Scleractinia Corals. mKO is commercially available with product name "mKO1" from Medical & Biological Laboratories Co., Ltd. and Amalgaam, Inc.

(B) Production of Fluorescence Emission Ability Quick-Acquiring Variant By Introduction of Point Mutation According to a predicted structure of mKO which is predicted based on its primary structure, several sites (points) of an mKO gene, which were seemingly capable of quickly acquiring fluorescence emission, were selected, and introduced with amino-acid substitution point mutation in such a manner that the fluorescent characteristic would be retained. Introduction of the amino-acid substitution point mutation was carried out by using an amino-acid substitution point mutation introduction primer and, as a template, an *E. coli* expression vector (pRSET B Invitrogen) inserted with the mKO gene. DNA thus introduced with the amino-acid substitution point mutation was treated in accordance with thermal cycling so that a template DNA was dissociated, the primer was annealed, and the primer elongation was performed repeatedly. Thus, the DNA was amplified. The primer used in amplification was phosphorylated at a 5' terminal.

(a) Phosphorylation of Primer at 5' Terminal
Incubated with the following for 30 minutes at 37° C.

| | |
|---|---|
| 100 μM primer | 2 μl |
| 10× T4 polynucleotide kinase buffer | 5 μl |
| 100 μM AMP | 0.5 μl |
| Sterilized water | 41.5 μl |
| T4 polynucleotide kinase (10 U/μl) | 1 μl |

(b) Point Mutation Introduction PCR

| | |
|---|---|
| 5' phosphorylated primer mix | final 4 μl |
| template (mKO-pRSET B) | 100 ng |
| 10× polymerase buffer | 2.5 μl |

| | |
|---|---|
| 10× DNA ligase buffer | 2.5 μl |
| 2.5 mM dNTPs | 1 μl |
| polymerase (pfu) 2.5 U/μl | 1 μl |
| Taq DNA ligase 40 U/μl | 0.5 μl |

A sterilized water was provided in an amount so that a total of amounts would be 50 μl.

Program
A thermal cycler was GeneAmp PCR system 9700.
Reaction Condition:
65° C. 5 min (ligation)
95° C. 2 min (denaturation)
95° C. 20 sec (denaturation)
52° C. 20 sec (annealing of the primer to the template)
65° C. 8 min (primer elongation and ligation)
Above 3 steps were carried out for 25 cycles.
75° C. 7 min (final elongation)
4° C. storing
Used Primer:

```
                                              (SEQ ID 1)
5'-cgcgtcacaatggccgasggcgggccaatgcct-3'

(SEQ ID 2)
5'-cgcgtcacaatggccragggcgggccaatgcct-3'

(SEQ ID 3)
5'-tacggccacagavtntttactaaatatcca-3'

(SEQ ID 4)
5'-aatcacaaatgccaannsaagactacttacaag-3'

(SEQ ID 5)
5'-cttaaaatgccaggagancattacatcagccat-3'

(SEQ ID 6)
5'-aacattactgagvwsgtagaagatgcagta-3'

(SEQ ID 7)
5'-tacaaggcggcaraaragattcttraaatgccagga-3'

(SEQ ID 8)
5'-gaccattacatcrrscatcgcctcgtcagg-3'
Mixed-Base Notation: w = a/t, r = a/g,
s = g/c, v = a/g/c, n = a/t/g/c
```

(c) DpnI Treatment

A sample subjected to the PCR was incubated with 1 μl of DpnI at 37° C. for 1 hour, so as to digest a template expression vector.

(d) Transformation into *Escherichia Coli*

*Escherichia coli* JM109 (DE3) was transfected with the sample thus processed with the DpnI treatment, so as to produce a transformant. The transformant expressing a fluorescent protein was compared with one another in terms of a fluorescent intensity, so as to pick up a candidate clone. An expression vector plasmid of a picked-up clone was purified by using Wizard Plus SV Minipreps DNA Purification System (Promega). Then, by using the expression vector plasmid as a template, introduction of amino-acid substitution point mutation was repeatedly carried out, so as to evolve mKO. Purification of the expression vector plasmid was carried out in accordance with a protocol for the kit.

(e) Determination of Base Sequence of mKO Variant

A transformant clone which was eventually selected out was incubated. An expression vector plasmid of the transformant clone was purified by using Wizard Plus SV Minipreps DNA Purification System (Promega). Purification of the expression vector plasmid was carried out in accordance with a protocol for the kit. A base sequence of an mKO variant in the purified expression vector plasmid was analyzed, so as to determine an amino acid sequence. In analysis of the base sequence, BigDye Terminator ver.1 Cycle Sequencing Kit (Applied Biosystems) was used. The analysis of the base sequence was carried out in accordance with a protocol for the kit. A result was that lysine (K), which was 49th in an mKO amino acid sequence, was substituted with glutamic acid (E), proline (P), which was 70th in the mKO amino acid sequence, was substituted with valine (V), phenylalanine (F), which was 176th in the mKO amino acid sequence, was substituted with methionine (M), lysine (K), which was 185th in the mKO amino acid sequence, was substituted with glutamic acid (E), lysine (k), which was 188th in the mKO amino acid sequence, was substituted with glutamic acid (E), serine (S), which was 192th in the mKO amino acid sequence, was substituted with aspartic acid (D), serine (S), which was 196th in the mKO amino acid sequence, was substituted with glycine (G), and leucine (L), which was 210th in the mKO amino acid sequence, was substituted with glutamine (Q). A variant of the above sequence was named mKO2. The base sequence of a fluorescent protein mKO2 is shown by SEQ ID 20 herein, and an amino acid sequence thereof is shown by SEQ ID 21 herein.

(f) Analysis of Fluorescent Characteristic

A recombinant protein of mKO2 fused with His-Tag, was expressed by using *Escherichia coli*, and then purified by using Ni-NTA Agarose (QIAGEN). Purification of the recombinant protein was carried out in accordance with a protocol for the kit. Respective absorbing spectra of solutions of 20 μM fluorescent protein, 150 mM KCl, and 50 mM HEPES-KOH pH7.4 were measured with a spectrophotometer (U-3310 HITACHI), and molar absorption coefficients were worked out from peak values of the respective absorbing spectra. mKO and mKO2 were dissolved into the 150 mM KCl and the 500 mM HEPES-KOH pH7.4 solution in such a manner that an absorbing value at 500 nm would be 0.005. Respective fluorescence spectra of mKO and mKO2 excited by light at 500 nm were measured with a fluorescence spectrophotometer (F-2500 HITACHI), and areas of the respective fluorescence spectra were worked out. Fluorescence quantum yield of mKO was set to 0.6, and fluorescence quantum yield of mKO2 was worked out according to a ratio of the areas. In order to work out pH sensitivity (pKa) of mKO2, 2 μl of an mKO2 protein solution (19.1 mg/ml) was added into 100 μl of the 100 mM buffer liquid, and then measured for an absorbing spectrum.

Buffer solutions of respective pH were as follows:

pH4, 5: acetic acid buffer solution pH6: phosphate buffer solution pH7, 8: HEPES buffer solution pH9, 10: glycine buffer solution.

Table 6 shows comparison of the fluorescent characteristic of mKO and that of mKO2.

Because an absolute brightness of a fluorescent protein molecule was expressed by a formula "molar absorption coefficient×quantum yield", an absolute brightness of mKO was 51600×0.6=30.9 k, and that of mKO2 was 63800×0.57=36.3 k. Thus, the absolute brightness of the fluorescent protein mKO2 was approximately 1.2 times brighter than that of mKO.

TABLE 6

|  | Excitation Maximum | Fluorescent Maximum | Molar Absorption Coefficient | Quantum yield | pH Sensitivity |
|---|---|---|---|---|---|
| mKO | 548 nm | 559 nm | 51600 (548 nm) | 0.60 | pKa = 5.0 |
| mKO2 | 551 nm | 565 nm | 63800 (551 nm) | 0.57 | pKa = 5.5 |

(g) Evaluation of mKO2 Expressed in Incubated Cell

From a fluorescent protein expression vector plasmid pmKO1-MN1 (Medical & Biological Laboratories Co., Ltd.), an mKO (mKO1) gene site was cut out by using restriction enzymes NotI and XbaI. Subsequently, the fluorescent protein expression vector plasmid pmKO1-MN1 was inserted alternatively with an mKO2 gene which was ligated with an NotI site at the 5' end and an XbaI site at the 3' end. Ligation of the restriction enzyme site sequences was carried out by a PCR. A thermal cycler was GeneAmp PCR system 9700.

Composition of PCR Reaction Liquid

| Template (mKO2-pRSET B) | 1 μl |
|---|---|
| ×10 pfu buffer | 5 μl |
| 2.5 mM dNTPs | 3 μl |
| 20 μM forward primer | 1 μl |
| 20 μM reverse primer | 1 μl |
| DMSO | 5 μl |
| Mili-Q | 33 μl |
| pfu polymerase (2.5 U/μl) | 1 μl |

PCR Reaction Condition

| 94° C. | 1 min (PAD) |
|---|---|
| 94° C. | 30 sec (denaturation) |
| 52° C. | 30 sec (annealing of a primer to a template) |
| 72° C. | 1 min (primer elongation) |
| Above 3 steps were carried out for 30 cycles. | |
| 72° C. | 7 min (final elongation) |
| 4° C. | storing |

```
Forward primer
                                             (SEQ ID 9)
5'-ataagaatgcggccgcggggaccatggtgagtgtgattaaaccag
ag-3'

Reverse primer
                                            (SEQ ID 10)
5'-cgctctagattaggaatgagctactgcatcttctacca-3'
```

Approximately 700 bp of an amplified band obtained by 1% agarose gel electrophoresis was cut out. The amplified band was then purified and subcloned into pmKO1-MN1 treated with the restriction enzymes NtoI and XbaI, so as to produce pmKO2-MN1. pmKO1-MN1 and a constructed expression vector plasmid pmKO2-MN1 were used in comparing fluorescent emission ability of mKO (mKO1) and that of mKO2 in a HeLa cell.

It was prepared such that HeLa cells in 35-mm glass bottom dishes would be 40% confluent. The HeLa cells were then introduced with pmKO1-MN1 or pmKO2-MN1 by use of a gene induction reagent, polyfect (QIAGEN), so as to express fluorescent proteins. Setting of a cell-culture condition and induction of the genes were carried out in accordance with a protocol for polyfect. 1 μg of the respective expression vector plasmids was used per 35-mm glass bottom dish.

In a time sequential manner, fluorescence images were acquired, and fluorescent brightness was compared to one another. The fluorescent images were acquired by use of an excitation filter 25BP520-540HQ, a fluorescent filter 25BA555-600HQ, and a dichroic mirror DM545HQ. For an excitation light, a xenon light source was used. Light from the xenon light source was irradiated for 0.5 second while 70% of the light was cut off (30% transmission). A microscope was an inverted microscope IX-71 (Olympus Co., Ltd), and a lens was 20× Uapo/340 N.A. 0.75 (Olympus Co., Ltd). For image acquisition and analysis, Metamolph (Nippon Roper Co., Ltd) was used in a mode set to binning 2. The fluorescence images were acquired with a cooling CCD camera ORCA-ER (Hamamatsu Photonics K.K).

After 6, 8, and 10 hours of introduction of the expression vector plasmids, fluorescence images were acquired, and fluorescence brightness was plotted by working out average brightness per cell (see FIG. 1). Because a model was not capable of controlling the expression, there were unevenness in a time length from intake of the expression vector plasmids to expression of the fluorescent proteins. However, a result was that clearly, (i) mKO2 acquired the fluorescence emission ability in a shorter time period and (ii) mKO2 emitted fluorescence two times or more brighter than did mKO1. Thus, a fluorescence emission ability quick-acquiring variant mKO2 was used in subsequent experiment.

(c) Construction of mKO2-Cdt1

Fluorescent protein mKO2 was amplified by a PCR in which primers 1 and 2 described below were used. Then, the amplified mKO2 was introduced into an EcoRI-EcoRV site of a pcDNA3 vector. Subsequently, a fragment of Cdt1 (Genbank Accession No.; NM_030928) was amplified by a PCR in which primers 3 and 4 described below were used in combination (by combinational use of the primers 3 and 4, a fragment corresponding to 30th to 100th amino acids of Cdt1 was amplified), or by a PCR in which primers 3 and 5 described below were used in combination (by combinational use of the primers 3 and 5, a fragment corresponding to 30th to 120th amino acids of Cdt1 was amplified). Then, the fragment of Cdt1 was introduced into an Xho I-XbaI site. Transferring into a lentivirus vector (CSII-EF-MCS) was carried out by using the EcoRI-XbaI site. Respective PCRs were carried out in the following condition.

Reaction liquid:

| Template DNA; | 1 to 10 ng/1 μl |
|---|---|
| 10× polymerase buffer | 10 μl |
| 2.5 mM dNTP mix; | 8 μl |
| forward primer (20 μM); | 1 μl |
| reverse primer (20 μM); | 1 μl |
| DMSO; | 5 μl |
| pfu porymerase 2.5 U/μl | 1 μl |
| Mili Q | 73 μl |

A thermal cycle was GeneAmp PCR system 9700.
Reaction Condition:

| 94° C. | 2 min |
|---|---|
| 94° C. | 1 min |
| 50° C. | 30 sec |
| 72° C. | 1.5 min |
| repeat the above 3 reactions for 28 cycles, and subsequently | |
| 72° C. | 7 min |
| 4° C. | storing |

(2) Construction of mAG-Geminin

Fluorescent protein mAG was a monomeric variant of Azami Green (AG) isolated from *Galaxea fascicularis* of Scleractinia Corals, and commercially available, as a product name mAG1, from Medical and Biological Laboratories Co., Ltd and Amalgaam, Inc.

mAG was amplified by a PCR in which primers 6 and 7 described below were used. Then, mAG was introduced into an EcoRI-EcoRV site of a pcDNA3 vector. Subsequently, a fragment of Geminin (Genbank Accession No.; NM_015895) was amplified by a PCR in which primers 8 and 9 described below were used (by use of the primer 8 and 9, a fragment corresponding to 1st to 110th amino acids of Geminin). Then, the fragment of Geminin was introduced into an Xho I-XbaI site. Transferring into a lentivirus vector (CSII-EF-MCS) was carried out by using an EcoRI-XbaI site. Respective PCRs were carried out in the following condition.

Reaction Liquid:

| | |
|---|---|
| Template DNA; | 1 to 10 ng/1 µl |
| 10× polymerase buffer | 10 µl |
| 2.5 mM dNTP mix; | 8 µl |
| forward primer (20 µM); | 1 µl |
| reverse primer (20 µM); | 1 µl |
| DMSO; | 5 µl |
| pfu porymerase 2.5 U/µl | 1 µl |
| Mili Q | 73 µl |

A thermal cycle was GeneAmp PCR system 9700.
Reaction Condition:

| | |
|---|---|
| 94° C. | 2 min |
| 94° C. | 1 min |
| 50° C. | 30 sec |
| 72° C. | 1.5 min |
| repeat the above 3 reactions for 28 cycles, and subsequently | |
| 72° C. | 7 min |
| 4° C. | storing |

Primer 1: mKO2 forward primer (M12-EcoN-F)
(SEQ ID 11)
5'-ggg gaa ttc gcc acc atg gtg agt gtg att aaa cca gag Prrimer 2: mKO2 reverse primer (m11-AGCter-EcoV-R)
(SEQ ID 12)
5'-atg gat atc cgc cct ggg aag gca aca ttg agt aat gag cta ctg cat ctt cta c Primer 3: XhoI-Hu.Cdt (30)(F):
(SEQ ID 13)
5'-gcc ctc gag ccc agc ccc gcc agg ccc gca Primer 4: Hu.Cdt (100) ter.XbaI (R):
(SEQ ID 14)
5'-gca tct aga tta ttt ctt tat ctt ctg gcc cgg aga Primer 5: Hu.Cdt (120) ter.XbaI (R):
(SEQ ID 15)
5'-gca tct aga tta gat ggt gtc ctg gtc ctg cgc Primer 6: mAG forward primer (hM12-EcoN-F):
(SEQ ID 16)
5'-ggg gaa ttc gcc acc atg gtg agc gtg atc aag ccc ga Primer 7: mAG reverse primer (hM12-EcoV-R):
(SEQ ID 17)

5'-atg gat atc cct tgg cct ggc tgg gca gca t

Primer 8: XhoI-Hu.Geminin (1)(F):
(SEQ ID 18)
5'-gcc ctc gag atg aat ccc agt atg aag cag aaa c Primer 9: Hu.Geminin (110) ter.XbaI (R):
(SEQ ID 19)
5'-gca tct aga tta cag cgc ctt tct ccg ttt ttc tgc Example 2

Transfection and Imaging

Cell Culturing Method

HeLa cells and COS7 cells were incubated in a DMEM into which a 10% fetal-bovine serum and penicillin/streptomycin were added. Mouse NMuMG mammary gland epithelial cells were incubated in a DMEM (high glucose) into which a 10% fetal-bovine serum, penicillin/streptomycin, and a 10 µg/ml insulin (sigma) were added. EGF and TGFβ1 were purchased from R&D Co., Ltd.

Transfection

The HeLa cells were transfected with a gene construct produced in Example 1, in accordance with a lipofectin method. A specific procedure for transfection of the gene construct was as follows. On a 35-mm glass bottom dish, the HeLa cells were incubated in a phenol red-free Dulbecco's Modified Eagle Medium containing a 10% bovine fetal serum (FBS). A liquid A (which contained 1 µg of plasmid and 100 µl of an Opti-MEM) and a liquid B (which contained 4 µl of lipofectin and 100 µl of an Opti-MEM) were prepared separately, and mixed with each other, so as to prepare a liquid mixture thereof. The liquid mixture was then left for 15 minutes at room temperature. A culture supernatant of the HeLa cells incubated on the 35-mm glass-bottom dish in advance was replaced with an Opti-MEM. Into a culture medium of the HeLa cells, the liquid mixture of the liquids A and B was added. After 4 hours, a culture supernatant was replaced with a new culture medium.

After 1 to 2 days, imaging was carried out by using an incubator microscope (Olympus Co., Ltd. LCV 100) for 24 to 60 hours, so as to screen HeLa cells in each of which a fluorescent signal was emitted in a cell cycle-specific manner in its nucleus. DIC images were acquired at Wavelength 1 (LED620 nm). An mKO2 fluorescent signal was collected at Wavelength 2 (ex: BP520-540HQ, em: BA555-600HQ). An mAG signal was collected at Wavelength 3 (ex: 470DF35, em: 510WB40).

Furthermore, after the transfection, the HeLa cells were incubated in a culture medium into which 500 µg/ml of G418 was added, and assessed for cytotoxicity by testing whether a clone of the HeLa cells could proliferate or not.

As a result, it was confirmed that in the case of transfection with (i) the fragment (hereinafter also referred to as mKO2-Cdt1#10) corresponding to 30th to 120th amino acids of Cdt1 and (ii) the fragment (hereinafter also referred to as mAG-Geminin#2) corresponding to 1st to 110th amino acids of Geminin, a cell cycle-specific nuclear fluorescent pattern was acquired, and no cytotoxicity was generated.

Respective base sequences of mKO2-Cdt1#10 and mAG-Geminin#2 thus produced have been deposited as AB370332 and AB370333 in DDBJ database.

Example 3

Production of Lentivirus and Transduction into Cell

Lentiviruses of mKO2-Cdt1 #10 and those of mAG-Geminin#2 were produced by use of HEK293 cells, and transduced into various cells. A specific procedure for transduction was as follows.

Production of Lentivirus

A procedure for production of the lentiviruses was developed by modifying a method developed by Dr. Miyoshi (Subteam for Manipulation of Cell Fate, Technology and Development for BioSignal Program, BioResource Center, RIKEN). Namely;

Liquid A;

| | |
|---|---|
| pCAG-HIVgp plasmid | 10 μg |
| pCMV-VSV-G-RSV-Rev plasmid | 10 μg |
| CSII-EF-MCS-mKO-Cdt1#10 or CSII-EF-MCS-mAG-Geminin#2 | 17 μg |
| Opti-MEM | 1.5 ml |

Liquid B;

| | |
|---|---|
| Lipofectamine 2000 | 36 μl |
| Opti-MEM | 1.5 ml |

The liquids A and B were prepared, and mixed with each other to produce a liquid mixture. The liquid mixture was then left at room temperature for 20 minutes. The HEK 293T cells were treated with trypsinization so as to be dissociated, and the number of the HEK 293T cells was counted. It was prepared such that the number of the HEK 293T cells would be $6 \times 10^6$ cells/5 ml. A 10 cm-dish was provided, in which 5 ml of a culture medium was poured and then the liquid mixture was added therein. Into this, 5 ml of the HEK 293T cells were added finally. The HEK 293T cells in the medium were incubated by an incubator under a condition of 5% $CO_2$ at 37° C. After 24 hours, the culture medium was replaced. After 2 days, a culture supernatant was collected so as to produce a virus fluid. The culture supernatant was centrifuged at a rotation speed of 3000 rmp for 5 minutes, so as to produce a supernatant which was then collected and dispensed. The supernatant was stored at −80° C. To the HEK 293T cells, a new culture medium was provided. After 3 days, a culture supernatant was collected in a same manner and stocked as a virus fluid.

Transduction into Cells

Figure 2:
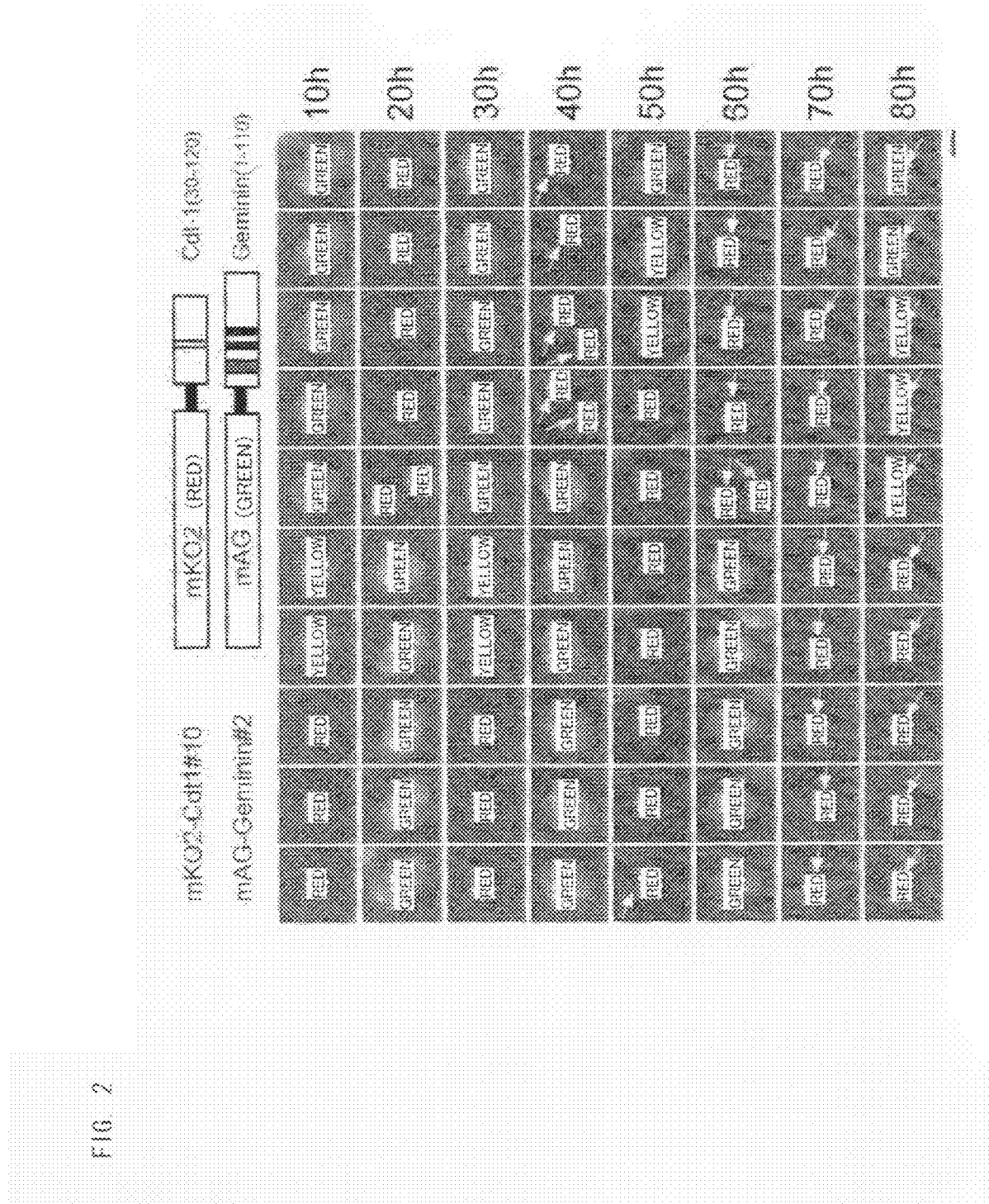
FIG. 2 shows images of a HeLa cell stably expressing Fucci, in which images a nucleus of the HeLa cell shows a fluorescent pattern corresponding to cell-cycle progression.

Arbitrary cells were provided. Into a culture supernatant of the cells adhering to or floating in a plastic dish, the virus fluid was added to roughly 30 to 300 μl/dish sized of 3.5 cm. After 2 to 3 days, when the cells were observed with a fluorescent microscope, it was possible to observe that the cells transduced (the cells being infected by a virus in the virus fluid and thereby having a genome integrated with a gene of the virus) emitted fluorescence. After 1 week of co-transduction with two viruses having mKO-Cdt1#10 and mAG-Geminin#2, respectively, single cell cloning of the cells was started. In approximately 4 weeks, the single cell replicated to form a colony emitting two colors of fluorescence. The colony was then collected so as to produce indicator-expression cells. FIG. 2 shows results obtained by observing clones of HeLa_LV_mKO-Cdt1#10 and mAG-Geminin#2 with the fluorescent microscope.

In accordance with the above manner, HeLa cells (cultured cells of human cervical cancer cells), HEK293 cells (cultured cells derived from human embryonic kidney cells), PC12 cells (cultured cells derived from rat pheochromocytoma), COS cells (cultured cells of monkey cells), CHO cells (cultured cells of a hamster), NmuMG cells (cultured cells of mouse cells), primary cultured cells of rat neuronal cells, primary cultured cells of mouse bone marrow-derived cells, and the like cells were co-transduced with two viruses (mKO2-Cdt1#10 and mAG-Geminin#2). Then, each of the cells thus co-transduced with genes of the respective viruses were imaged. It was observed that in each of the cells, fluorescence by mKO was localized in a cell nucleus in a resting phase (G1 phase), whereas fluorescence by mAG was localized in the cell nucleus in a proliferating phase (S, G2, and M phases). Those members of the PC12, COS cell, NMuMG cell which expressed both indicators were cloned by single cell cloning, so as to obtain several cell lines.

For concrete examples, FIG. 2 shows the results obtained from imaging the HeLa cells each being co-transduced with two kinds of lentiviruses (mKO2-Cdt1#10 and mAG-Geminin#2) and thus introduced with genes of the respective lentiviruses. A cell cycle period was presumably variable due to differences in cell density and/or serum concentration. Because green fluorescence rapidly disappeared just before the end of the M phase and red fluorescence became detectable in the early $G_1$ phase, a small gap in fluorescence indicated existence of a newborn daughter cell. On the other hand, while the fluorescence was changed from a red color to a green color, red and green fluorescence overlap each other so as to yield a yellow color in the nucleus. In order to examine whether a timing of color change correlated with the onset of the S phase or not, transformants were pulse-labeled with BrdU for 5 minutes, and immunostained for BrdU immediately after pulse-labeling. C of FIG. 3 shows typical confocal images of the HeLa cells at G1/S transition and in the $G_1$ phase, the S phase, the $G_2$ phase and the M phase. Because all the HeLa cells emitting yellow fluorescence in their nuclei showed incorporation of BrdU, emergence of the green fluorescence was indicative of the onset of the S phase. Similar results were obtained from separate experiments in each of which the HeLa cells were immunostained for PCNA. Thus, the HeLa cells emitting pure green fluorescence in their nuclei were observed. Such HeLa cells were either in the S phase or the $G_2$ phase, and distinguishable by nuclear BrdU immunostaining or PCNA immunostaining. These results showed that mKO2-Cdt1#10 accumulated in the $G_1$ phase, whereas mAG-Geminin#2 accumulated in the S/$G_2$/M phase. Such fluorescent ubiquitination-based cell cycle indicators were named "Fucci". Analysis of DNA content by flow cytometry revealed that Fucci-expressing HeLa cells and parent HeLa cells show the same distribution (see D of FIG. 3, left). The Fucci-expressing cells were divided into populations each emitting red fluorescence (mKO2(+) mAG(−)), yellow fluorescence (mKO2(+) mAG(+)), or green fluorescence (mKO2(−) mAG(+)) (see D of FIG. 3, center). DNA context of each population was stained by Hoechst 33342, and then analyzed. The Fucci-expressing cells emitting green or yellow fluorescence had fully- and partially-replicated complements of DNA, respectively (D of FIG. 3, right). On this regard, differential profiling of cells at $G_1$ phase and S/$G_2$/M phase can be achieved by (i) sorting a population of cells emitting red, yellow, or green fluorescence and (ii) examining various cellular functions, such as gene expression and antigen surface expression.

Example 4

Immunocytochemical Cell Cycle Analysis

Analytical Method

Fucci-expressing HeLa cells were incubated on a cover glass, and treated with BrdU (sigma) at 37° C. for 5 minutes. After being washed with PBS(−), the Fucci-expressing HeLa cells were fixed by 4% PFA at 4° C. for 10 minutes, and then treated with 0.1% TritonX-100/PBS(−) at room temperature for 5 minutes.

Antibodies used were goat anti-mouse IgG conjugated with Alexa Fluor 633 (Molecular Probe), mouse anti-BradU mAb (Immunological Direct), and mouse anti-PCNA mAb (Dako). Images were acquired with FV 500 (Olympus Co., Ltd) confocal microscope system equipped with a 488-nm laser line (Ar), a 543-nm laser line (He/Ne), and a 633-nm laser line (He/Ne).

Flow Cytometry

Hoechst 33342 (56 µl of a 1 mg/ml stock) (DOJINDO Laboratories) was added to a 10-cm dish containing the parent HeLa cells or the Fucci-expressing HeLa cells. After incubation for 30 minutes, incubated cells were collected, and analyzed by using a BD™ LSR (Becton, Dickinson and Company Co., Ltd). mKO 2 and mAG were excited by a 488-nm laser line (Ar) and Hoechst 33342 was excited by a 325-nm laser line (HeCd). Fluorescent signals were collected at 530 nm (through 530/28 BP) (FL 1) for mAG, at 575 nm (through 575/26 BP) (FL 2) for mKO 2, and at 400 nm (through 380 LP) (FL 5) for Hoechst 33342. Data were analyzed by using FlowJo software (Tree Star, Inc).

Monitoring Result of Structural and Behavioral Changes and Cell-Cycle Dynamics of Cultured Cell Epithelial-mesenchymal transition (EMT) is a fundamental morphogenetic process by which a mesenchymal cell is formed from an epithelium during embryonic development, wound repair, and tumor progression in a multicellular tissue. In vitro, EMT is characterized by dissolution of a cell-cell junction, cytoskeletal rearrangement, and an increased motility of a cultured cell. A specific stage of a cell cycle may be involved in the process. Actually, a transforming growth factor β (TGFβ) efficiently induces EMT in an AML-12 hepatocyte synchronized at the $G_1/S$ phase, but is inactive in the AML-12 hepatocyte synchronized at the $G_2/M$ phase. Further, an NMuMG cell undergoes EMT in response to the TGFβ. In order to study the cell cycle progression during EMT, NMuMG cells which were transformed stably and expressed Fucci were examined.

Figure 4:
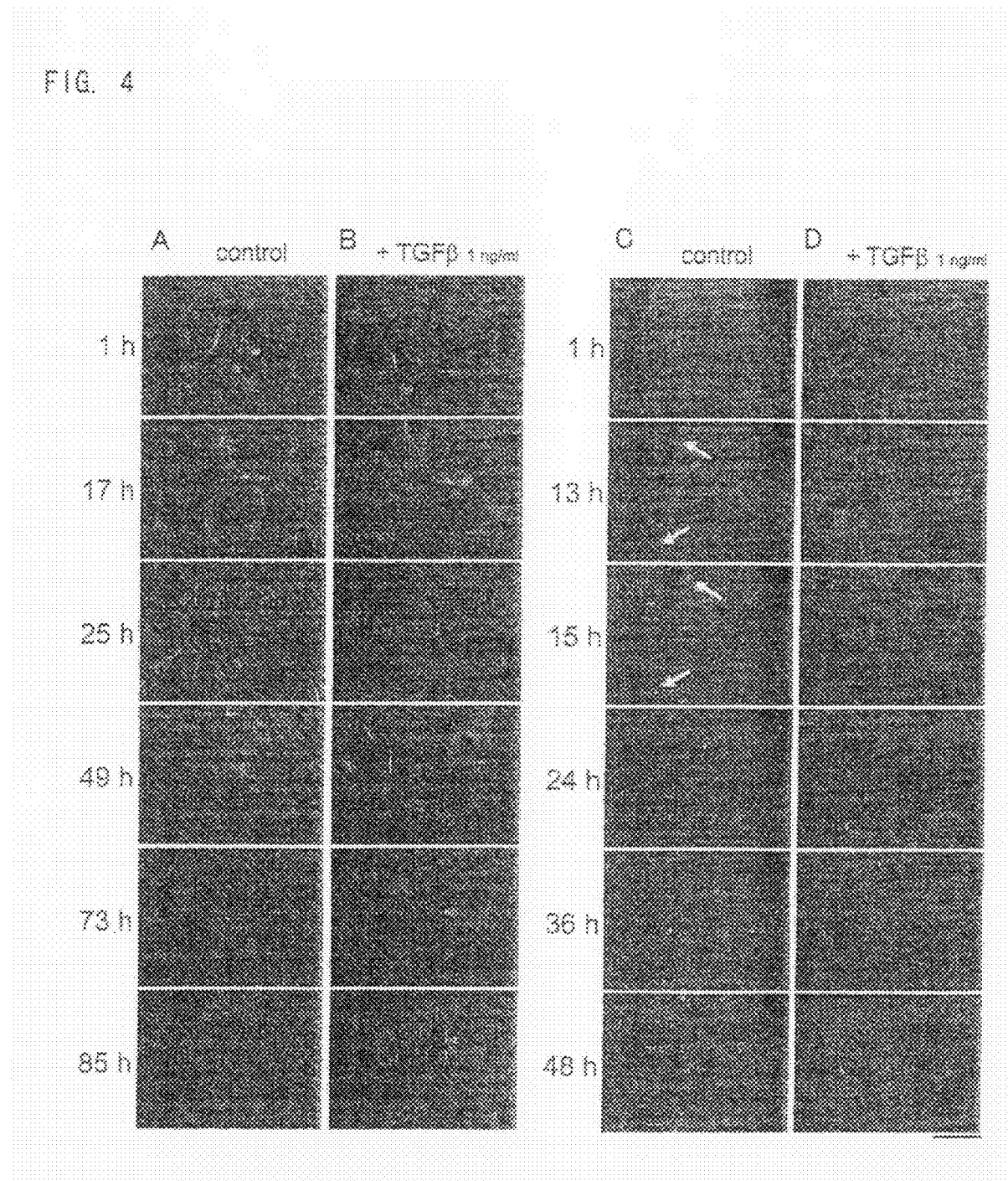
FIG. 4 shows monitoring results of behavioral changes of and cell-cycle dynamics of the cell stably expressing Fucci.
Figure 5:
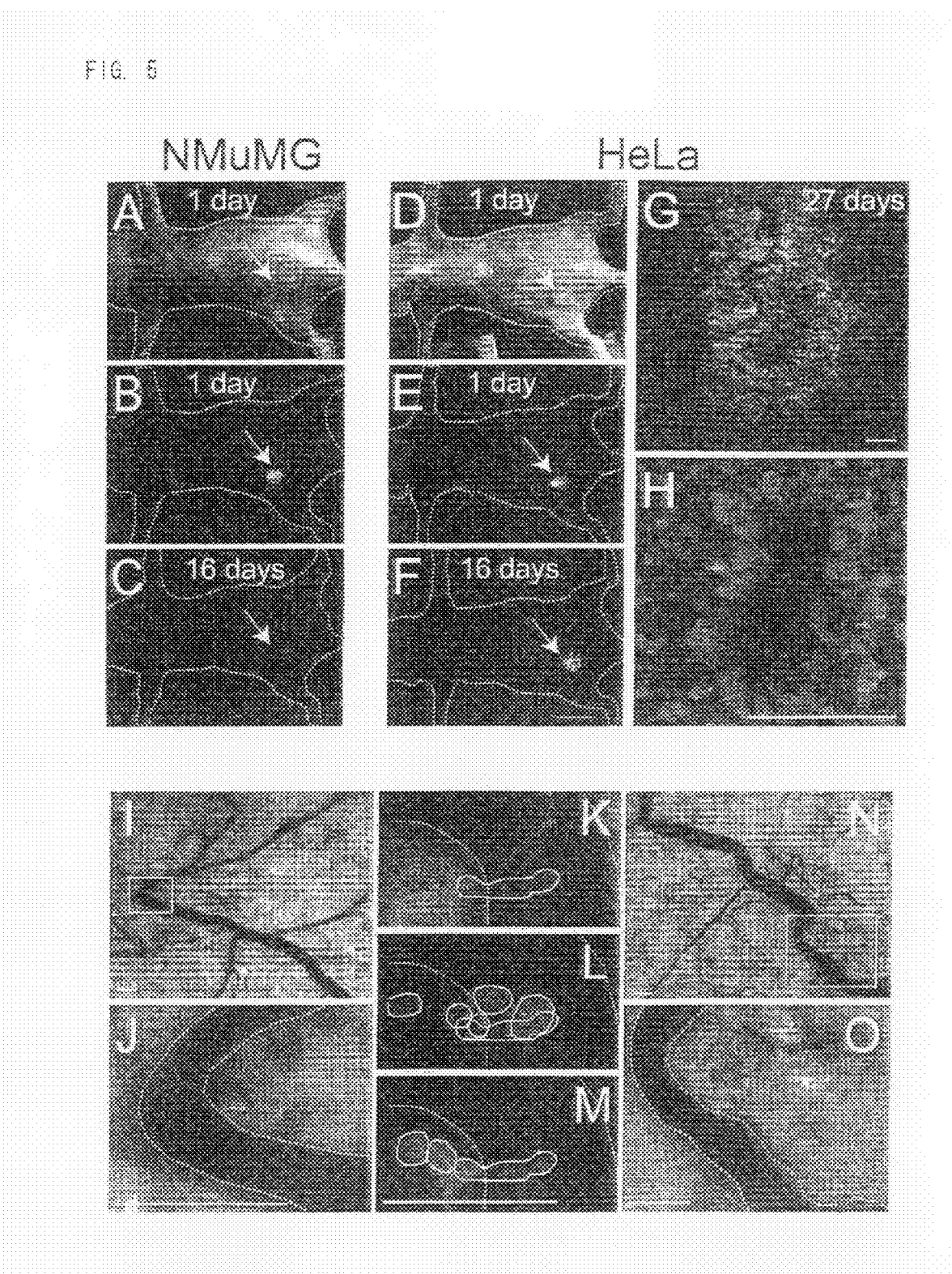
FIG. 5 shows results obtained by monitoring, by marking with the Fucci probe, cell-cycle progression of a tumor cell in a live mouse.

Cells were dispersed on a cover glass. Subsequently, the cells proliferated and adhered to neighboring ones, so as to form a cluster (FIG. 4A, 1h). It was evidenced that these cells had high proliferation ability, by proliferation images in each of which cells emitting green fluorescence in their nuclei were dominant (FIG. 4A, 25h to 49h). However, at confluence, the cells emitting green fluorescence in their nuclei were not seen any more, and replaced with those expressing red fluorescence in their nuclei (FIG. 4A, 73h). This indicated that the cells remained in the $G_1$ phase. When a wound was introduced into the confluent monolayer (FIG. 4C, 1h), cells along the wound started emitting green fluorescence (C of FIG. 4, 13h, arrow). This indicated that the NMuMG cells were required to proliferate due to introduction of the wound. After 9 to 13 hours of the introduction of the wound, cells emitting green fluorescence in their nuclei appeared remarkably. Such a time delay of more than 8 hours was reproducibly observed in other similar wound healing experiments and was reminiscent of an 8-hour interval required for an NIH 3T3 cell to re-enter a cell cycle from a state of quiescence ($G_0$) after the onset of a proliferation stimulus. Thus, it might be a case that the confluent NMuMG cells remained in the $G_0$ phase (A of FIG. 4, 85h). Next, same experiments were carried out in the presence of 1 ng/ml TGFβ. Within 1 day of treatment with TGFβ, cells emitting green fluorescence in their nuclei were increased in number. This indicated that this ligand induced a $G_1/S$ transition (B of FIG. 4, 1h through 49h). Subsequently, each of the cells begun to adopt a spindle-shaped, fibroblast-like morphology and high motility (B of FIG. 4, 49h). After 2 days of the treatment with TGFβ, the cells emitting fluorescence in their nuclei were decreased in number. This reflected a $G_1$ arrest effect of TGFβ (B of FIGS. 4, 49h to 85h). Thus, the cells treated with TGFβ spread without proliferation, in contrast with untreated NMuMG cells which were densely packed in a confluent monolayer. In addition, introduction of the wound did not result in proliferation, but rather in a further expansion of the cells (D of FIG. 4).

Example 5

Production of Transgenic Animal

Plasmids each prepared by incorporating mKO-Cdt1#10 and mAG-Geminin#2 into respective pCAGGS vectors were named pCAGGS_mKO-Cdt1#10 and pCAGGS_mAG-Geminin#2. By use of the respective plasmids, a fragment to be injected into a mouse egg cell was produced.

| | |
|---|---|
| pCAGGS_mKO-Cdt1#10 or pCAGGS_mAG-Geminin#2 | 20 µg/40 µl |
| 10× H buffer | 10 µl |
| H₂O | 50 µl |

Restriction enzymes Sal I, Pst I, Pvu I

Reaction liquids above were mixed with each other, and incubation was carried out at 37° C. for 2 hours. Bands were extracted by electrophoresis, and then 3.2 Kb of a band was purified for mKO-Cdt1#10, while 3.3 kb of a band was purified for mAG-Geminin#2. Production of a transgenic mouse was outsourced to the Research Resource Center, Brain Science Institute, Riken. As a result of genotyping, 16 lines of transgenic mice having genes for mKO-Cdt1#10 and 8 lines of transgenic mice having genes for mAG-Geminin#2 were obtained.

Example 6

Cell-Cycle Progression of Tumor Cell in Live Mouse

Whole-Body Imaging of Mice (i) Subcutaneous and intravenous injection of a cultured cell and (ii) whole imaging with OV100 (Olympus Co., Ltd) were carried out as described in a document by Hoffman, Yang, et al. (Nat. Protocol, 3. pp 1429-1438. 2006). In order to visualize a blood vessel, Angio Sense-IVM750 (VisEn Medical, Inc) was injected, or an endothelial cell was stained by using anti-CD31 mAb (Chemicon, Inc).

By use of a CAG promoter, transgenic mouse lines expressing mKO2-Cdt1#10 were produced. Of the 16 lines of transgenic mice emitting Red fluorescence, #596 was chosen for further characteristic analysis. Further, 8 lines of green fluorescence mAG-Geminin#2 mice were produced, of which #504 was chosen for further characteristic analysis. Such mouse lines provided an unprecedented model with which to study coordination of a cell cycle and development. #504 was particularly useful because it provided in vivo information on a proliferation pattern. During early development of a mammalian cerebral cortex, neural progenitors in a ventricular zone (VZ) continuously proliferated. In order to determine whether mAG-Geminin#2 green fluorescence was emitted by the neural progenitors, a #504 transgenic mouse embryo aged an embryonic day (E) 14 was treated with immunohistochemistry on telencephalic sections. Because telencephalic cells having green nucleus were immunopositive for Nestin but not MAP 2, these cells could be neural progenitors.

The #596 transgenic mouse and the #504 transgenic mouse were crossbred with each other so as to generate a mouse line producing Fucci in which every somatic cell nucleus exhibited either red or green fluorescence.

E13 Fucci (#596/#504) embryos were perfused transcardially with a fixative (4% PFA), placed in an ice-cold fixative for 2 hours, cryoprotected in a PBS containing 20% sucrose, and embedded in an OCT compound. Coronal head sections (each of which had a thickness of 15 µm) were imaged by using FV100 equipped with two laser diodes (473 nm and 559 nm). Images were put together so as to create wide-filed pictures. Brain sections from an E14#504 embryo was fixed, and incubated with mouse antiMAP2 mAb (Chemicon, Inc) or mouse anti-Nestin mAb (PharMingen, Inc). The brain sections from the E14#504 embryo was then incubated with goat anti-mouse IgG conjugated with AlexaFluor 546X (Molecular Probes, Inc).

Imaging Method of Cultured Brain Slice

Brain slices were prepared from Fucci-expressing mice (#596/#504) at E13, and cultured in a collagen gel as described in Miyata et al. (J. Neurosci. Res. 69, pp 861-868. 2002). The brain slices were exposed to 5% $CO_2$ and 40% $O_2$. 3D imaging was carried out in an xyz-t mode by using FV1000 multiposition stage system. A recording interval was 10 minutes. At each time point, 20 confocal images along a z-axis (2 µm step) were acquired. In order to avoid crossdetection of green and red fluorescence signals, the images were sequentially acquired at 488 nm (Ar) and 543 nm (He/Ne). Green and red fluorescence images were merged for each confocal image. Image registration and proper alignment of FV1000 equipped with the two laser lines and a detection channels were verified by using double-labeled fluorescent beads (TetraSpeck Fluorescent Microsphere Standards, diameter of 0.5 µm, Molecular Probes, Inc). Data analysis was carried out by using Velocity software (Improvision, Inc) and METAMORPF software (Universal Imaging, Media, Pa.).

Monitoring Result of Cell-Cycle Progression of Tumor Cell in Live Mouse

Whole-body imaging and intravital cellular imaging of mice injected with cultured tumor cells genetically labeled with fluorescent proteins were powerful techniques for investigating tumor development. Fucci-expressing NMuMG cells were subcutaneously injected into mammary glands of nude mice, so as to use Fucci in monitoring tumor development (A of FIG. 5). After 1 day of injection, both cells emitting green fluorescence and cells emitting red fluorescence were observed (B of FIG. 5). After 16 days, however, only the cells emitting red fluorescence were seen (C of FIG. 5). This indicated that NMuMG cells stopped proliferating. Next, Fucci-expressing HeLa cells were injected into nude mice in a similar manner (D of FIG. 5). Each of the injected HeLa cells grew gradually, and stably emitted either green or red fluorescence, thereby indicating tumor progression (E and F of FIG. 5). After 27 days of the injection, expanded mass was observed through a skin under a microscope (Olympus Co., Ltd. IV100, 10×, UplanFL N N.A.=0.30) (G of FIG. 5).

Well-developed tumor mass was visualized by being loaded with AngioSense 750, which emitted far-red fluorescence. Although triple-color live imaging identified HeLa cells in the $G_1$ phase and the $S/G_2$ phase, their positions relative to the tumor mass were not clear due to a low spatial resolution. The tumor was fixed, sectioned, and stained with an antibody against CD31. Both the red and green fluorescence of Fucci remained after conventional immunostaining procedures which included fixation in 4% PFA. A cell-cycle phase pattern of HeLa cells around blood vessels was clearly visualized (H of FIG. 5). The pattern appeared to depend on several factors, including maturity of the mass and a degree of necrosis in surrounding tissues.

Next, cell-cycle progression of tumor cells was examined during initial steps of a classic metastatic cascade, such as (i) adhesion to endothelial cells and (ii) extravasation and metastasis. Fucci-expressing HeLa cells in a gel were injected into a skin vein, and intravital cellular imaging was carried out. Interestingly, at early stages, nearly all of the HeLa cells attached to an inner wall of veins were in the $G_1$ phase (I and J of FIG. 5). A cell in the process of extravasation and metastasis was imaged (K, L, and M of FIG. 5). Within a cluster of HeLa cells across a vein wall, an elongated cell emitting yellow fluorescence in a fragmented nucleus was observed to pass through the vein wall. After 4 days of injection, HeLa cells were found to invade tissues and proliferate therein (N and O of FIG. 5). This indicated that extravasation and metastasis were repeated plural times.

Previous work showed that cultured cells with differentially labeled cytoplasm and nuclei, which cultured cells were to be injected into mice, could be used in imagining nuclear-cytoplasmic dynamics in order to monitor cancer cell tracking, cell death in live mice, deformation, extravasation and metastasis, and mitosis. In combination with such cytoplasmic labeling techniques, fluorescence imaging of Fucci-expressing cells which are stably transformed and introduced into live animals will provide reliable pharmacodynamic readouts for growth and metastatic behavior of tumors.

Figure 6:
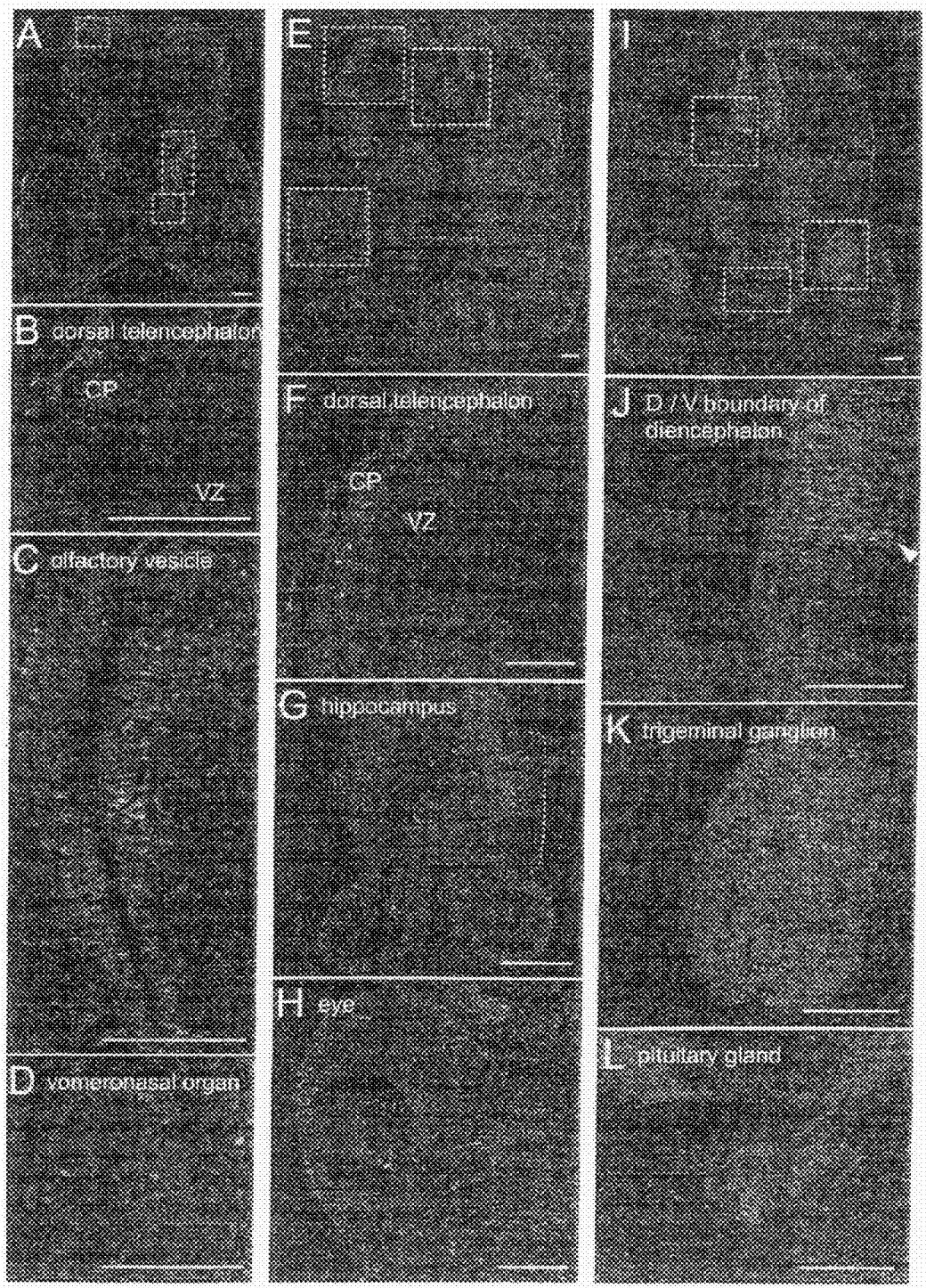
FIG. 6 shows results of cell-cycle analysis of generation of a neural tissue in a Fucci transgenic mouse.
Figure 7:
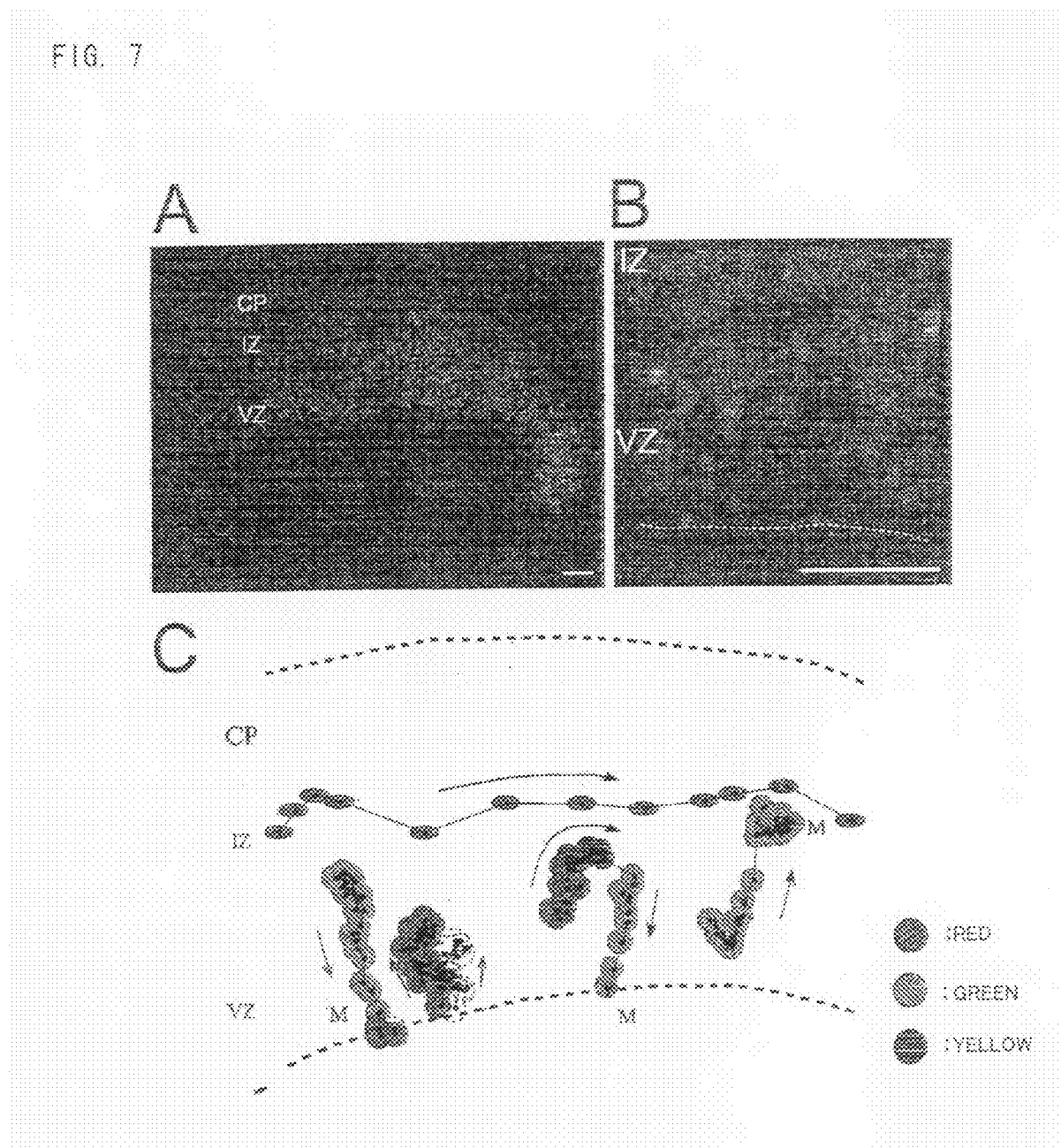
FIG. 7 shows results of a time-lapse imaging experiment in which a slice of brain primordium of an E13 Fucci transgenic mouse embryo is used.
Figure 8:
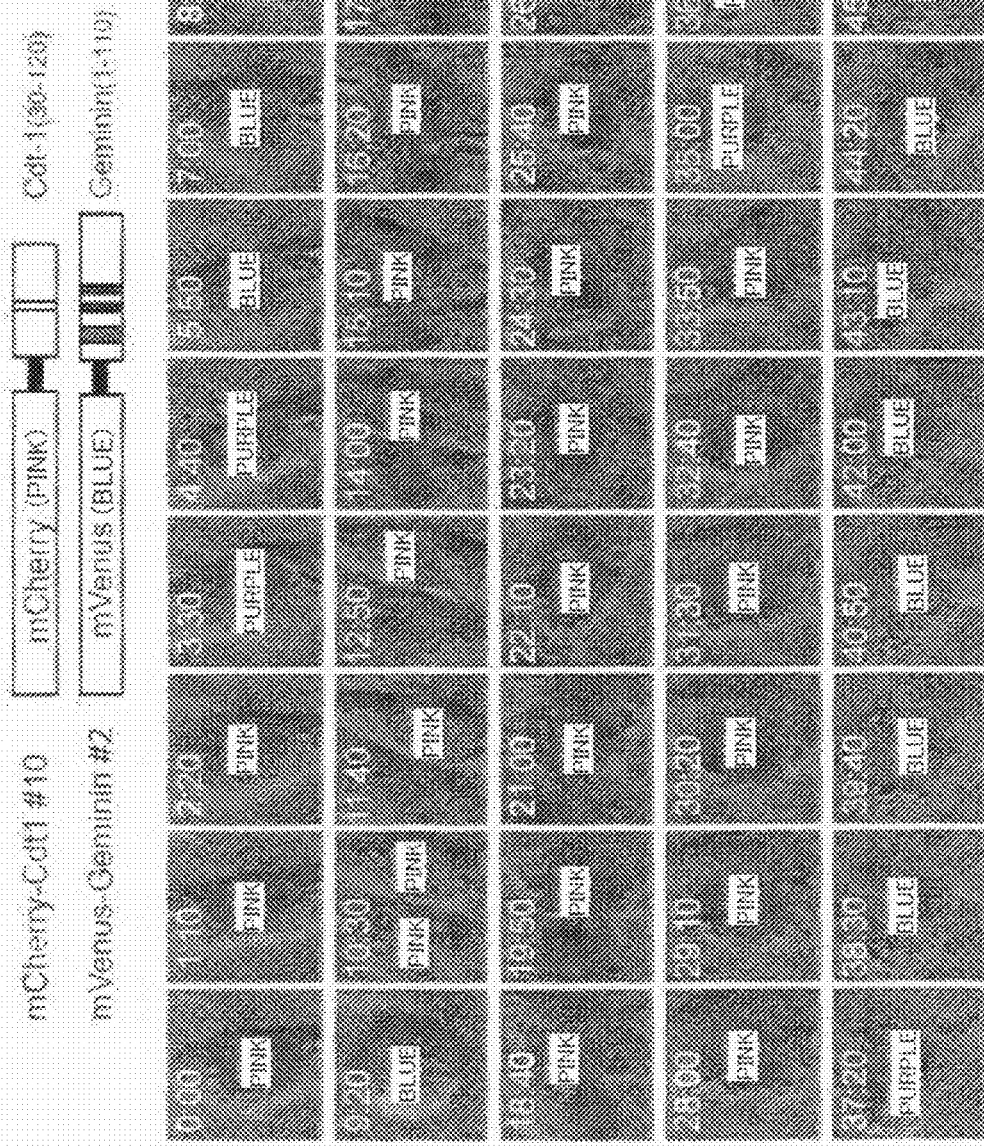
FIG. 8 shows images of a PC12 cell stably expressing next-generation Fucci (mCherry-Cdt1#10 and mVenus-Geminin#2).
Figure 9:
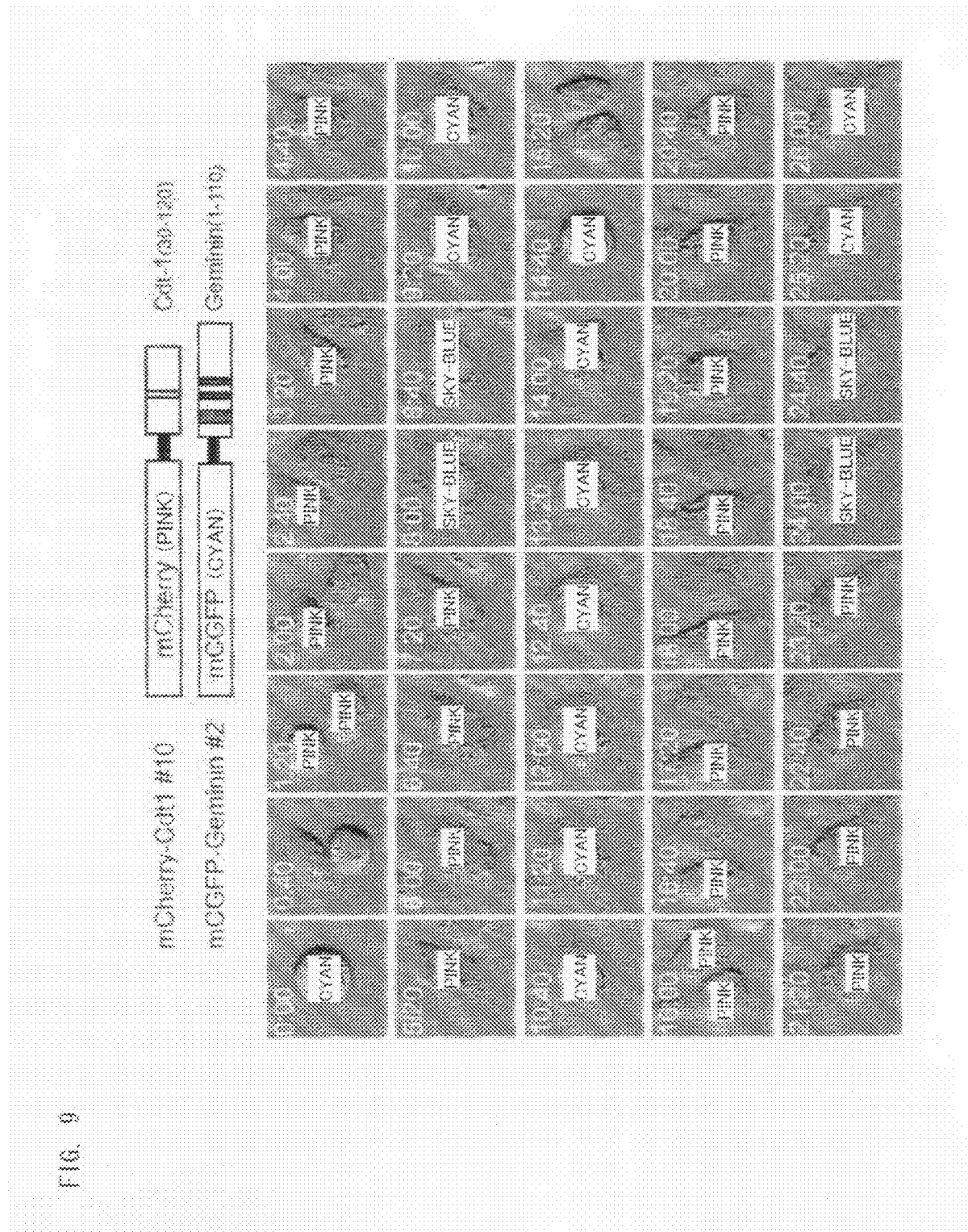
FIG. 9 shows images of a HeLa cell stably expressing a next generation Fucci (mCherry-Cdt1#10 and mCGFP-Geminin#2).

Result of Cell-Cycle Analysis of Developing Neural Tissue in Fucci Transgenic Mouse One major advantage of a genetically encoded probe is that it need not depend on transcriptional regulation; its transcription can be driven by using constitutive promoters. Thus, transgenic organism for cell-cycle analysis can be easily generated. An E13 Fucci transgenic mouse embryo was fixed, and coronal sections of its brain were prepared. Red or greed fluorescence was examined in every section by using confocal scanning microscope. A, E, and I of FIG. 6 show fluorescence images of three representative sections. Red and green signals appeared to be well balanced at an embryonic stage, but an overall ratio of green-to-red signal decreased as the mouse grew.

In a developing cerebral cortex, (B, F, G, and J of FIG. 6), nuclei emitting red mKO2-Cdt1#10 fluorescence were identified in two main cell populations: which were post-mitotic neurons capable of populating different layers in a cortical plate (CP), and mitotic neural progenitors in a VZ. The post-mitotic neurons exhibited much brighter red fluorescence, probably due to accumulation of mKO2-Cdt1#10 after cell-cycle exit. Nuclei in blood vessels exhibiting bright red were visualized in the VZ (B and F of FIG. 6). In a diencephalon, there was a stripe of cells in the $G_1$ phase, which stripe of cells corresponded to zona limitans intrathalamica (zli). A dorsal thalamus contained more green nuclei than did a ventral thalamus (I and J of FIG. 6). This suggested that cells in a ventral region undergo cell-cycle exit for differentiation prior to those in a dorsal region.

A differential intensity of red fluorescence between mitotic cells and post-mitotic cells was observed also in a developing neuroepithelial of an olfactory system and a vomeronasal system (C and D of FIG. 6, respectively) as well as a developing neuroepithelial of a retina (H of FIG. 6). Random distribution of high- and low-intensity fluorescent nuclei might suggest that respective architectures of an olfactory epithelium and a vomeronasal epithelium were not yet established at E13. In contrast, bright red nuclei were observed in a central apical region of a developing retina (H of FIG. 6), whose developing retina ganglion cells were to undergo centrifugal differentiation. Epithelial cells of a lens had also exited the cell cycle by this stage. Other extra-neural tissues with bright red fluorescence included a trigeminal ganglion (k of FIG. 6) and a pituitary gland (L of FIG. 6).

Geminin and Cdt1 are previously shown to be abundantly expressed by neural progenitors during early mouse neurogenesis, but transcriptionally downregulated at late development stages. Fucci signal is not affected by transcriptional regulation in transgenic mice.

In the developing cerebral cortex, some neural progenitors exit the cell cycle and migrate beyond the VZ, where they differentiate into neurons or, at later stages, into ganglion cells. Neural progenitors also undergo a typical migration pattern within the VZ; their nuclei undergo characteristic movements, known as interkinetic nuclear movements. Nuclei in the M phase are localized on the ventricular surface, whereas nuclei in the S phase migrate to the ventricular zone. In order to observe spatial and temporal regulation of proliferation, differentiation, and migration of neural progenitors, a time-lapse imaging experiment was carried out in which slices of a dorsal telencephalon prepared from an E 13 Fucci transgenic mouse embryo were used (A of FIG. 7). The time-lapse imaging experiment in which cortical slices are used is usually acquired at 0.3 hours or longer intervals. With such long intervals, neither nuclear movements nor cell-cycle progression can be monitored adequately. However, the bright Fucci fluorescence enables 3D time-lapse imaging with 10 minutes intervals in an xyz-t mode by using FV1000 multi-position stage system. At each time point, 20 confocal images along a z-axis (2 μm step) were acquired. In addition, exposure of slices to 40% oxygen (instead of usual exposure to 20%) had significantly improved cell proliferation, differentiation, and migration during imaging experiment. As mentioned earlier, the red fluorescence of neural progenitors nuclei observed immediately after mitosis was much dimmer than was red fluorescence of differentiated neural cells nuclei. In order to visualize migration of the nuclei in the cell cycle within the VZ, photomultiplier tube (PMT) sensitivity for red fluorescence was increased. While nuclei in the CP showed saturated red fluorescence, nuclei in the VZ exhibited equivalent levels of either green or red fluorescence (B of FIG. 7). Under such conditions, it was possible that change in a color between green and red during cell cycle progression and migration of cells were clearly followed.

Trajectories of neural progenitor nuclei corresponding to interkinetic nuclear movements were followed. C of FIG. 7 (left) shows a successive trajectory of a migrating cell, in which the cell in the S phase and near a subventricular zone (IZ) underwent the $G_2$ phase, migrated to the ventricular zone (VZ), and underwent the M phase there to divide itself into two $G_1$ cells through cell division. The two $G_1$ cells in the post-mitotic phase emitted red, and started migrating away from the ventricular surface. Other cells exhibited so-called elevator movement (C of FIG. 7, center), in which they rose toward the subventricular zone during the $G_1$ phase, made a hairpin turn in the subventricular zone at timing of the $G_1/S$ phase, and migrated to the ventricular surface during the S phase. It was known that many of the cells undergo the mitotic phase in the ventricular surface, whereas several percent of the cells undergo the mitotic phase also in the subventricular zone. Latter ones of the cells were able to be imaged (C of FIG. 7, right). Also, a phenomenon in which red nuclei quickly traveled across the subventricular zone was imaged eventually. Such nuclei were likely to belong to cortical GABA (γ-amino-butyric-acid) neurons, which are known to be born in subpallial telencephalon of archaic humans and to migrate tangentially to reach their final destination.

Nuclear localization of Fucci is advantageous in the following respects. In order to identify a cell type and observe cell morphology, additional far-red fluorescent proteins (mCherry, mKeima, and the like) spectrally distinct from both mAG and mKO2 are tagged with Nuclear Export Signal (NES) and expressed in cytoplasm. This makes it possible to distinguish the additional far-red fluorescent proteins. A third color of a fluorescence signal can also be provided by a chemical dye. In experiment shown in FIG. 7, clear DiD crystals were placed on a pial surface of a brain slice so as to sparsely label progenitors connecting cranial pia mater. This was an example in which it was possible to identify bipolar morphology of a progenitor, the progenitor having a green nucleus whose movement was tracked (data are not shown).

By expressing a FRET indicator, such as cameleon and Raichu-Ras, in cytoplasm, it is possible to understand a cell cycle in parallel with intracellular events (data are not shown). For example, when a Fucci-expressing COS7 cell was transfected with Raichu-Ras, it was verified that Ras was more active in the $G_1$ phase than in the $S/G_2$ phase in response to an epidermal growth factor (EGF) signal. Thus, cell-cycle dependency of plural intracellular events can be elucidated without using cell-cycle synchronization techniques. Multi-color imaging in combination with such fluorescent probes and proteins will further expand the application of the Fucci technology.

The Fucci technology allows dual-color imaging, thereby making it possible to distinguish actual cells in the $G_1$ phase from those in the $S/G_2/M$ phase. The Fucci technology allows in-vivo analysis of spatial and temporal patterns of cell-cycle dynamics, owing to brightness and high contrast of two colors (red and green) of fluorescence. Although Fucci is composed of mKO2-Cdt1#10 and mAG-Geminin#2, transfection of either one of them is sufficient in obtaining a cell-cycle indicator function. For example, the transgenic mouse line #504 produces mAG-Geminin#2, but still provides in vivo information on proliferation patterns. However, coexpression of both constructs is still considerably more useful because it highlights the $G_1/S$ transition with a yellow signal, and because it allows continuous tracking of migrating cells or nuclei in the cell cycle. In this regard, reliable gene-transfer technique by which stoichiometry of two constructs is controlled is necessary.

Further research were made so as to attain objects including (1) production of developed Fucci (FIGS. 8 and 9), which was different from that using mKO2 and mAG in combination, (2) a development of probe capable of visualizing a cell-cycle phase other than the $G_1/S$ transition, and (3) development of a Fucci derivative which functioned in a non-mammalian individual. Such research benefited from exploration of molecular mechanisms underlying both cell-cycle progression and ubiquitin-mediated protein degradation. Regarding the objects, it was notable that a primary structure of Cdt1 and Geminin varied among species. By tagging mKO2 or mAG to certain domain of the two proteins (Cdt1 and Geminin) each having a lower homology among eukaryote, a derivative of Fucci which functioned in a fish cell and an insect cell was developed. Further, transgenic zebrafish and a *Drosophila* line expressing non-mammalian Fucci were developed, so as to investigate spatial and temporal regulation of cell-cycle progression during major morphogenetic events such as gastrulation and metamorphosis, and during basic morphogenetic processes such as invagination, involution, and branching.

Example 7

Screening of Anticancer Agent by Using Fucci Probe

Figure 10:
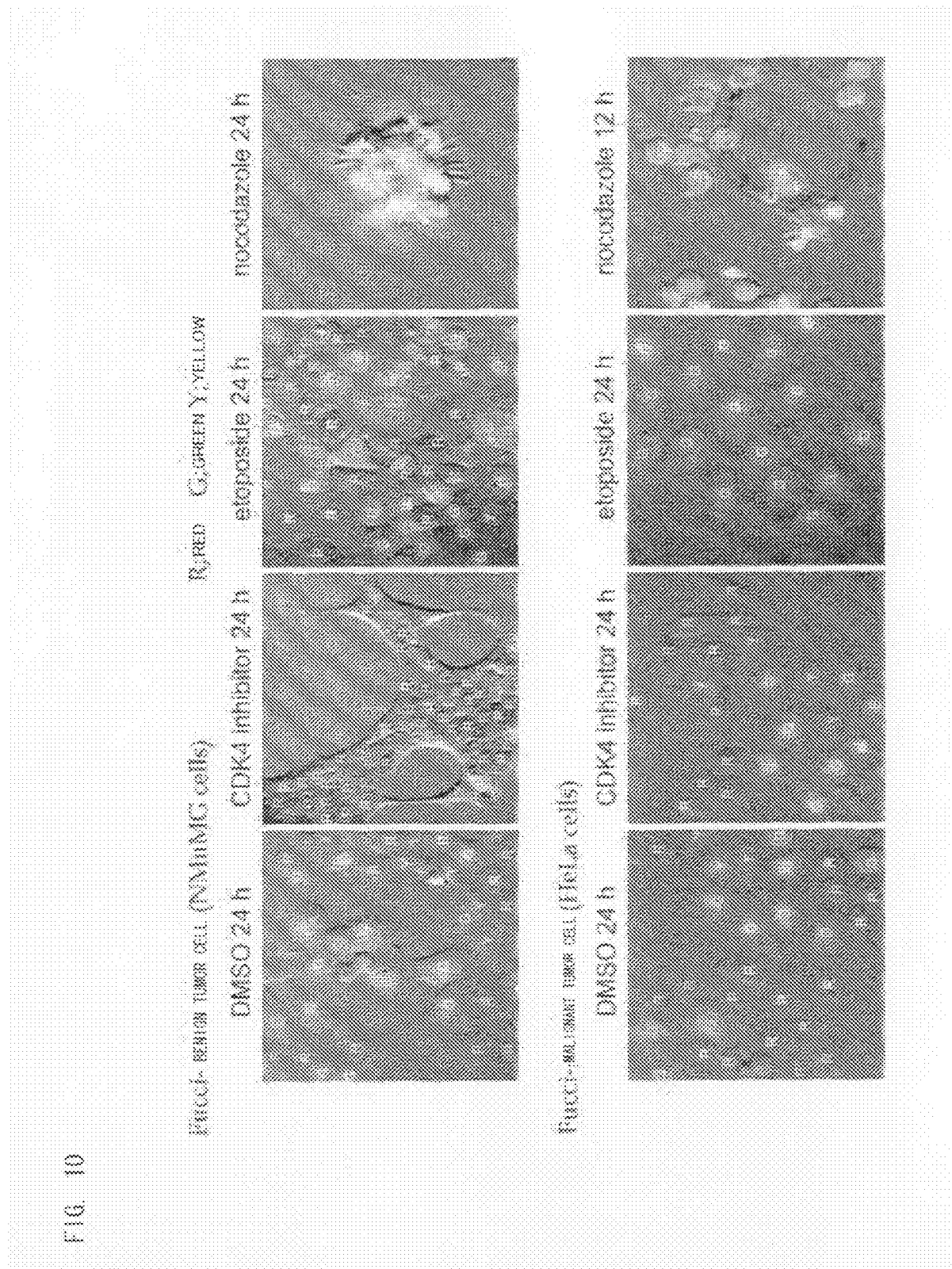
FIG. 10 shows results of screening anticancer agents by using Fucci probe.

Benign tumor cells (NMuMG cells) stably expressing Fucci and Malignant tumor cells (HeLa cells) stably expressing Fucci were used in observing reaction to an anticancer agent (FIG. 10). Data obtained from cells (control group) treated with DMSO treatment showed mixture of a red color and a green color, thereby indicating normal proliferation. A CDK4 inhibitor ($G_1$-phase inhibitor) sufficiently worked on the benign tumor cell, the NMuMG cells, while being ineffective to the malignant tumor cells, the HeLa cells. Etoposide (inhibitor of topoisomerase 2) sufficiently worked on the malignant tumor cell and thereby caused cell-cycle arrest at the $S/G_2$ phase, while having strong effect to the NMuMG cells and thereby induced apotosis. By Nocodazole (M-phase inhibitor), all the cells were arrested in a rounded state at the M phase.

(Distribution Source of Material)

DNA constructs of mKO2-Cdt1#10 and mAG-Geminin#2, their stable transformant cell lines, and transgenic mouse lines described herein will be distributed with concomitant purchase of cDNA for mKO2 or mAG from MB International Corp (Amalgaam, Ltd) (http://www.mblintl.com/mbli/index.asp).

The invention claimed is:

1. A method for performing phase identification of a cell cycle, the method comprising the steps of:
   visualizing, by respectively using markers, at least two or more gene-expression products whose amounts in a cell change in a cell-cycle dependent manner; and
   detecting the markers to distinguish a proliferation phase of the cycle from a resting phase of the cycle,
   wherein the at least two or more gene-expression products are co-expressed in a cell and comprise
   (i) a first gene-expression product comprising a partial fragment of Cdt1; wherein the partial fragment of Cdt1 excludes a Geminin binding site, and increases in a G1 phase and decreases in an S/G2/M phase; and
   (ii) a second gene-expression product comprising a partial fragment of Geminin; wherein the partial fragment of Geminin excludes a Cdt1 binding site, and decreases in the G1 phase and increases in the S/G2/M phase;
   wherein the first gene-expression product and the second-gene expression product are labeled by the markers, and the markers are different from each other, to visualize the first gene-expression product and the second gene-expression product.

2. The method as set forth in claim 1, wherein the first gene-expression product is the partial fragment of Cdt1, which partial fragment of Cdt1 is composed of 30th through 120th amino acids of Cdt1.

3. The method as set forth in claim 1, wherein the second gene-expression product is the partial fragment of Geminin, which partial fragment of Geminin is composed of 1st through 110th amino acids of Geminin.

4. The method as set forth in claim 1, wherein the markers are a fluorescent protein or a luminescent protein.

5. The method as set forth in claim 1, wherein the markers are detected over time by carrying out a time-lapse imaging observation on a living cell or a living tissue.

6. The method as set forth in claim 1, wherein the first gene-expression product is labeled by a red fluorescent protein as the marker, and the second gene-expression product is labeled by a green fluorescent protein as the marker.

7. The method as set forth in claim 1, wherein the first gene-expression product is a product in which $1^{st}$ through $30^{th}$ amino acids of Cdt1 are further excluded.

8. The method as set forth in claim 1, further comprising
   introducing into a cell (i) a first gene construct for encoding the first gene-expression product and the marker, and (ii) a second gene construct encoding the second gene-expression product and the marker, and
   causing the first and second gene constructs respectively to express the first gene-expression product and marker labeling the first gene-expression product, and the second gene-expression product and marker labeling the second gene-expression product.

9. A method for screening a cell-cycle inhibitor or a drug for a cell cycle-related disease or a method for examining a compound, a drug, or a reagent on its effect and a functional mechanism, the method comprising the steps of:
   incubating a cell in the presence of a candidate substance for the cell-cycle inhibitor, a candidate substance for the drug for the cell cycle-related disease, or a reagent for inhibiting specific gene expression; and
   performing phase identification of a cell cycle in accordance with a method as set forth in claim 1, so as to select a candidate substance which has an influence on the cell cycle and/or cell death.

\* \* \* \* \*

SEQUENCE LISTING

```
<160> NUMBER OF SEQ ID NOS: 21

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 1
cgcgtcacaa tggccgasgg cgggccaatg cct                                  33

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 2
cgcgtcacaa tggccraggg cgggccaatg cct                                  33

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA
<220> FEATURE:
<221> NAME/KEY: misc_feature
<222> LOCATION: (15)
<223> OTHER INFORMATION: n stands for any base

<400> SEQUENCE: 3
tacggccaca gavtntttac taaatatcca                                      30

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: Synthetic
      DNA
<220> FEATURE:
<221> NAME/KEY: misc_feature
```

```
<222> LOCATION: (16)..(17)
<223> OTHER INFORMATION: n stands for any base

<400> SEQUENCE: 4
aatcacaaat gccaannsaa gactacttac aag                               33

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Synthetic
      DNA
<220> FEATURE:
<221> NAME/KEY: misc_feature
<222> LOCATION: (18)
<223> OTHER INFORMATION: n stands for any base

<400> SEQUENCE: 5
cttaaaatgc caggaganca ttacatcagc cat                               33

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 6
aacattactg agvwsgtaga agatgcagta                                   30

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 7
tacaaggcgg caraaragat tcttraaatg ccagga                            36

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 8
gaccattaca tcrrscatcg cctcgtcagg                                   30

<210> SEQ ID NO 9
<211> LENGTH: 47
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 9
ataagaatgc ggccgcgggg accatggtga gtgtgattaa accagag                47

<210> SEQ ID NO 10
<211> LENGTH: 38
<212> TYPE: DNA
```

```
<213> ORGANISM: Artificial Sequence
<220> FEATURE:
<223> OTHER INFORMATION: Description of Artificial Sequence: Synthetic
      DNA

<400> SEQUENCE: 10
cgctctagat taggaatgag ctactgcatc ttctacca                              38

<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 11
ggggaattcg ccaccatggt gagtgtgatt aaaccagag                             39

<210> SEQ ID NO 12
<211> LENGTH: 55
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 12
atggatatcc gccctgggaa ggcaacattg agtaatgagc tactgcatct tctac           55

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 13
gccctcgagc ccagccccgc caggcccgca                                       30

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 14
gcatctagat tatttcttta tcttctggcc cggaga                                36

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 15
gcatctagat tagatggtgt cctggtcctg cgc                                   33

<210> SEQ ID NO 16
<211> LENGTH: 38
<212> TYPE: DNA
<213> ORGANISM: Artificial Sequence
<220> FEATURE:
```

<223> OTHER INFORMATION: Description of Artificial Sequence: Synthetic
      DNA

<400> SEQUENCE: 16
ggggaattcg ccaccatggt gagcgtgatc aagcccga                               38

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 17
atggatatcc cttggcctgg ctgggcagca t                                     31

<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 18
gccctcgaga tgaatcccag tatgaagcag aaac                                  34

<210> SEQ ID NO 19
<211> LENGTH: 36
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 19
gcatctagat tacagcgcct ttctccgttt ttctgc                                36

<210> SEQ ID NO 20
<211> LENGTH: 654
<212> TYPE: DNA
<213> ORGANISM: Artificial Sequence
<220> FEATURE:
<221> NAME/KEY: CDS
<222> LOCATION: (1)..(654)
<223> OTHER INFORMATION: Description of Artificial Sequence: Recombinant
      DNA

<400> SEQUENCE: 20

```
atg gtg agt gtg att aaa cca gag atg aag atg agg tac tac atg gac       48
Met Val Ser Val Ile Lys Pro Glu Met Lys Met Arg Tyr Tyr Met Asp
1               5                   10                  15 ggc tcc gtc aat ggg cat gag ttc aca att gaa ggt gaa ggc aca ggc       96
Gly Ser Val Asn Gly His Glu Phe Thr Ile Glu Gly Glu Gly Thr Gly
            20                  25                  30 aga cct tac gag gga cat caa gag atg aca cta cgc gtc aca atg gcc      144
Arg Pro Tyr Glu Gly His Gln Glu Met Thr Leu Arg Val Thr Met Ala
        35                  40                  45 gag ggc ggg cca atg cct ttc gcg ttt gac tta gtg tca cac gtg ttc      192
Glu Gly Gly Pro Met Pro Phe Ala Phe Asp Leu Val Ser His Val Phe
    50                  55                  60 tgt tac ggc cac aga gta ttt act aaa tat cca gaa gag ata cca gac      240
Cys Tyr Gly His Arg Val Phe Thr Lys Tyr Pro Glu Glu Ile Pro Asp
65                  70                  75                  80 tat ttc aaa caa gca ttt cct gaa ggc ctg tca tgg gaa agg tcg ttg      288
```

```
Tyr Phe Lys Gln Ala Phe Pro Glu Gly Leu Ser Trp Glu Arg Ser Leu
            85                  90                  95 gag ttc gaa gat ggt ggg tcc gct tca gtc agt gcg cat ata agc ctt      336
Glu Phe Glu Asp Gly Gly Ser Ala Ser Val Ser Ala His Ile Ser Leu
                100                 105                 110 aga gga aac acc ttc tac cac aaa tcc aaa ttt act ggg gtt aac ttt      384
Arg Gly Asn Thr Phe Tyr His Lys Ser Lys Phe Thr Gly Val Asn Phe
            115                 120                 125 cct gcc gat ggt cct atc atg caa aac caa agt gtt gat tgg gag cca      432
Pro Ala Asp Gly Pro Ile Met Gln Asn Gln Ser Val Asp Trp Glu Pro
        130                 135                 140 tca acc gag aaa att act gcc agc gac gga gtt ctg aag ggt gat gtt      480
Ser Thr Glu Lys Ile Thr Ala Ser Asp Gly Val Leu Lys Gly Asp Val
145                 150                 155                 160 acg atg tac cta aaa ctt gaa gga ggc ggc aat cac aaa tgc caa atg      528
Thr Met Tyr Leu Lys Leu Glu Gly Gly Gly Asn His Lys Cys Gln Met
                165                 170                 175 aag act act tac aag gcg gca aaa gag att ctt gaa atg cca gga gac      576
Lys Thr Thr Tyr Lys Ala Ala Lys Glu Ile Leu Glu Met Pro Gly Asp
            180                 185                 190 cat tac atc ggc cat cgc ctc gtc agg aaa acc gaa ggc aac att act      624
His Tyr Ile Gly His Arg Leu Val Arg Lys Thr Glu Gly Asn Ile Thr
        195                 200                 205 gag cag gta gaa gat gca gta gct cat tcc                              654
Glu Gln Val Glu Asp Ala Val Ala His Ser
    210                 215

<210> SEQ ID NO 21
<211> LENGTH: 218
<212> TYPE: PRT
<213> ORGANISM: Artificial Sequence
<220> FEATURE:
<223> OTHER INFORMATION: Description of Artificial Sequence: Recombinant
      protein

<400> SEQUENCE: 21

Met Val Ser Val Ile Lys Pro Glu Met Lys Met Arg Tyr Tyr Met Asp
1               5                   10                  15

Gly Ser Val Asn Gly His Glu Phe Thr Ile Glu Gly Glu Gly Thr Gly
            20                  25                  30

Arg Pro Tyr Glu Gly His Gln Glu Met Thr Leu Arg Val Thr Met Ala
        35                  40                  45

Glu Gly Gly Pro Met Pro Phe Ala Phe Asp Leu Val Ser His Val Phe
    50                  55                  60

Cys Tyr Gly His Arg Val Phe Thr Lys Tyr Pro Glu Glu Ile Pro Asp
65                  70                  75                  80

Tyr Phe Lys Gln Ala Phe Pro Glu Gly Leu Ser Trp Glu Arg Ser Leu
                85                  90                  95

Glu Phe Glu Asp Gly Gly Ser Ala Ser Val Ser Ala His Ile Ser Leu
            100                 105                 110

Arg Gly Asn Thr Phe Tyr His Lys Ser Lys Phe Thr Gly Val Asn Phe
        115                 120                 125

Pro Ala Asp Gly Pro Ile Met Gln Asn Gln Ser Val Asp Trp Glu Pro
    130                 135                 140

Ser Thr Glu Lys Ile Thr Ala Ser Asp Gly Val Leu Lys Gly Asp Val
145                 150                 155                 160

Thr Met Tyr Leu Lys Leu Glu Gly Gly Gly Asn His Lys Cys Gln Met
                165                 170                 175

Lys Thr Thr Tyr Lys Ala Ala Lys Glu Ile Leu Glu Met Pro Gly Asp
```

-continued

```
             180                 185                 190
His Tyr Ile Gly His Arg Leu Val Arg Lys Thr Glu Gly Asn Ile Thr
         195                 200                 205

Glu Gln Val Glu Asp Ala Val Ala His Ser
     210                 215
```